US008128890B2

(12) United States Patent
Droog et al.

(10) Patent No.: US 8,128,890 B2
(45) Date of Patent: *Mar. 6, 2012

(54) METHODS AND ALGORITHMS FOR CELL ENUMERATION IN A LOW-COST CYTOMETER

(75) Inventors: Erik Droog, Delft (NL); Dhanesh Gohel, Levittown, PA (US); Arjan G. J. Tibbe, Deventer (NL); Jan Greve, Oldenzaal (NL); Leon W. M. M. Terstappen, Amsterdam (NL)

(73) Assignee: Veridex, LLC, Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/917,000

(22) Filed: Nov. 1, 2010

(65) Prior Publication Data
US 2011/0044527 A1    Feb. 24, 2011

Related U.S. Application Data

(62) Division of application No. 10/903,798, filed as application No. PCT/US03/04468 on Feb. 14, 2003, now Pat. No. 7,943,397.

(60) Provisional application No. 60/357,170, filed on Feb. 14, 2002.

(51) Int. Cl.
*G01N 33/52* (2006.01)
*G01N 33/553* (2006.01)

(52) U.S. Cl. ............ 422/417; 422/402; 422/67; 422/73; 422/82.08; 422/82.09; 422/554; 436/518; 436/526; 435/7.2; 435/288.3; 382/128; 382/133; 382/145; 382/149

(58) Field of Classification Search ............... 435/7.2, 435/287.2, 288.3; 436/518, 526; 422/402, 422/417, 67, 73, 82.08, 82.09, 554; 382/128, 382/133, 145, 149
See application file for complete search history.

(56) References Cited

U.S. PATENT DOCUMENTS
4,115,535 A    9/1978 Giaever et al.
(Continued)

FOREIGN PATENT DOCUMENTS
WO    98/28622 A1    7/1998
(Continued)

OTHER PUBLICATIONS

"Fluorescence staining and flow cytometry for monitoring microbial cells", Journal of Immunological Methods 243 (2000) pp. 191-210.

*Primary Examiner* — Gail R Gabel

(57) ABSTRACT

The enumeration of cells in fluids by flow cytometry is widely used across many disciplines such as assessment of leukocyte subsets in different bodily fluids or of bacterial contamination in environmental samples, food products and bodily fluids. For many applications the cost, size and complexity of the instruments prevents wider use, for example, CD4 analysis in HIV monitoring in resource-poor countries. The novel device, methods and algorithms disclosed herein largely overcome these limitations. Briefly, all cells in a biological sample are fluorescently labeled, but only the target cells are also magnetically labeled. The labeled sample, in a chamber or cuvet, is placed between two wedge-shaped magnets to selectively move the magnetically labeled cells to the observation surface of the cuvet. An LED illuminates the cells and a CCD camera captures the images of the fluorescent light emitted by the target cells. Image analysis performed with a novel algorithm provides a count of the cells on the surface that can be related to the target cell concentration of the original sample. The compact cytometer system provides a rugged, affordable and easy-to-use technique, which can be used in remote locations.

8 Claims, 18 Drawing Sheets

U.S. PATENT DOCUMENTS

| | | |
|---|---|---|
| 5,018,209 A | 5/1991 | Bacus |
| 5,073,857 A | 12/1991 | Peters et al. |
| 5,077,806 A | 12/1991 | Peters et al. |
| 5,186,827 A | 2/1993 | Liberti et al. |
| 5,287,272 A | 2/1994 | Rutenberg et al. |
| 5,340,749 A | 8/1994 | Fujiwara |
| 5,374,531 A | 12/1994 | Jensen |
| 5,466,574 A | 11/1995 | Liberti et al. |
| 5,556,764 A | 9/1996 | Sizto et al. |
| 5,579,531 A | 11/1996 | Sugita |
| 5,641,072 A | 6/1997 | Otake |
| 5,665,582 A | 9/1997 | Kausch et al. |
| 5,698,271 A | 12/1997 | Liberti et al. |
| 5,766,944 A | 6/1998 | Ruiz |
| 5,789,152 A | 8/1998 | Black |
| 5,985,153 A | 11/1999 | Dolan et al. |
| 6,013,532 A * | 1/2000 | Liberti et al. .................. 436/526 |
| 6,097,485 A | 8/2000 | Lievan |
| 6,101,265 A | 8/2000 | Bacus et al. |
| 6,136,182 A | 10/2000 | Dolan et al. |
| 6,221,607 B1 | 4/2001 | Tsipouras et al. |
| 6,251,615 B1 | 6/2001 | Oberhardt |
| 6,274,386 B1 | 8/2001 | Harttig |
| 6,316,215 B1 | 11/2001 | Adair et al. |
| 6,365,362 B1 | 4/2002 | Terstappen |
| 6,418,236 B1 | 7/2002 | Ellis |
| 6,620,591 B1 * | 9/2003 | Dunlay et al. ................. 435/7.2 |
| 6,623,982 B1 * | 9/2003 | Liberti et al. .................. 436/526 |
| 6,660,159 B1 * | 12/2003 | Terstappen et al. ............ 210/94 |
| 6,682,940 B2 | 1/2004 | Pankowsky |
| 6,861,259 B2 | 3/2005 | Columbus |
| 6,890,426 B2 | 5/2005 | Terstappen |
| 6,893,881 B1 | 5/2005 | Fodstad |
| 6,967,328 B2 | 11/2005 | Kienzle |
| 7,011,794 B2 | 3/2006 | Kagan |
| 7,042,769 B2 | 5/2006 | Yamauchi et al. |
| 7,764,821 B2 * | 7/2010 | Coumans et al. ............. 382/133 |
| 7,943,397 B2 | 5/2011 | Tibbe |
| 2004/0023222 A1 | 2/2004 | Russell et al. |
| 2009/0061476 A1 | 3/2009 | Tibbe et al. |
| 2009/0061477 A1 | 3/2009 | Tibbe et al. |

FOREIGN PATENT DOCUMENTS

| | | |
|---|---|---|
| WO | 99/08233 A1 | 2/1999 |
| WO | PCT/US00/02034 A1 | 1/2000 |
| WO | 0045169 A9 | 8/2000 |
| WO | WO 0045169 | 8/2000 |
| WO | PCT/US02/04124 A1 | 1/2002 |
| WO | WO 0278540 | 1/2002 |
| WO | 02065103 A1 | 8/2002 |
| WO | 03/069421 A2 | 8/2003 |
| WO | 2005008225 A1 | 1/2005 |
| WO | 2005008226 A1 | 1/2005 |
| WO | 2005005259 A1 | 6/2005 |
| WO | 2005059549 A1 | 6/2005 |
| WO | 2005062059 A1 | 7/2005 |
| WO | 2005095925 A1 | 10/2005 |
| WO | 2006014056 A1 | 2/2006 |

* cited by examiner a b

METHODS AND ALGORITHMS FOR CELL ENUMERATION IN A LOW-COST CYTOMETER

CROSS REFERENCE TO RELATED APPLICATIONS

This application is a divisional application of U.S. Ser. No. 10/903798 filed 30 Jul. 2004, now U.S. Pat. No. 7,943,397, which is the U.S. national stage of PCT/US03/04468, filed 14 Feb. 2003, which claims the benefit of claim priority under 35 U.S.C. 365(c) to U.S. Provisional Application No. 60/357,170, filed 14 Feb. 2002, all incorporated by reference herein.

FIELD OF THE INVENTION

This invention relates generally to simple and low cost electronic optical devices, methods and algorithms for enumeration of microscopic particles distributed in a two-dimensional plane. The novel counting techniques are particularly applicable to enumerating is magnetically selected fluorescent cells in complex biological specimens such as blood by means of an inexpensive cell cytometer.

BACKGROUND OF THE INVENTION

The enumeration of absolute levels of cells and their subsets in body fluids is of primary importance in determining the state of health of human beings and mammals in general. The primary analytical platform for performing such analyses is flow cytometry in which the specimen is either injected directly or after prior enrichment in rare cell analysis. Flow cytometry and similar complex analytical systems remain largely inaccessible for routine clinical use in resource-poor countries due to high instrument and reagents costs, lack of technical support, lack of robustness requiring frequent service, and the need for AC power. There is a clear need for simpler, more compact and less expensive systems also operable with emergency DC battery power and preferably exhibiting comparable performance characteristics.

In addition to the above-cited full sized flow cytometry systems available from Becton Dickinson and Beckman-Coulter, these vendors also sell scaled down less expensive versions, which still suffer from the other cited limitations. Similar limitations apply to the compact CyFlow® from Partec GmbH, (Munster, Germany) and to the Guava Personal Cytometer (Burlingame, Calif.). U.S. Pat. No. 6,097,485 (assigned to Integrated Wave Guides, Brookings, S. Dak.) discloses an ultra-miniature personal flow cytometer (pFCM) claimed to be of lower cost, but still exhibiting rather complex, electronic circuitry, optical designs, data reduction, all of which contribute to unacceptable complexity for a third world setting. All these systems use the flow concept, which obviously complicates the instrumental design. These scaled down versions of flow cytometry systems do not meet the clear need for a truly simple, compact, rugged, battery-operable and affordable cell analyzer.

Among the numerous clinical applications for a simple cell analyzer, counting of CD4 cells in HIV, granulocytes and platelets in patients treated with chemotherapy, and leukocytes in blood bags are most important. The current systems and methods for cell analysis have some significant disadvantages. They generally require sophisticated techniques, which involve the use of instruments that are expensive both in terms of initial cost and maintenance as well as requiring highly trained personnel. This makes the conventional systems unsuitable for use in laboratories of resource-poor countries.

Therefore, a low-cost, easy-to-use method, for example, for CD4 cell enumeration is needed. Such a method may serve as a compact alternative to the current cell analysis systems that would be suitable for physician practices, bedside testing, or in open field settings.

HIV and AIDS are the leading cause of death in Africa and the fourth leading cause of death worldwide. In the countries most affected, life expectancy has declined by 10 years and infant death rates have doubled. In countries with the highest HIV prevalence, such as Botswana, South Africa, and Zimbabwe, the full impact of the epidemic has not yet been felt because those infected recently have not yet developed overt symptoms. Equally important is the effect of HIV deaths on families, social systems, and national growth and development. Young adults who contribute substantially to the countries' gross domestic product are most commonly affected. The most effective intervention therapy for persons infected with HIV is the use of a combination of antiretroviral agents. However, the high cost of these regimens and the infrastructure needed to monitor their use have put these medications beyond the reach of most HIV-infected persons. Although the price of these drugs has fallen, making treatment a possibility for a greater number of persons, infrastructures to support the effective use of these medications remain inadequate and need strengthening. To characterize disease in an individual for purposes of estimating prognosis and planning therapy, clinicians need to know how far the disease has progressed.

In HIV disease, currently this is most usefully indicated by the CD4 count. HIV infects the CD4 positive subset of T-lymphocytes, eventually leading to their depletion and the onset of the various opportunistic infections manifested in AIDS. During the course of HIV infection, the number of CD4+ T-lymphocytes drops from the normal value of about 500 to 1300 cells/µl to less than 200 cells/µl. The natural course of HIV in a typical untreated patient begins with a sharp rise of virus in the blood and a consequent drop in CD4+ T-cells. The immune system soon recovers to some extent, however, and keeps HIV levels fairly steady for several years. Eventually, though, the virus gains the upper hand. AIDS is diagnosed when the CD4+ T-cell level drops below 200 cells per cubic millimeter of blood or when opportunistic infections (reflecting failed immunity) arise, whichever happens first. CD4+ T-cell levels can thus be used to determine the progression of the HIV disease. Furthermore, routine monitoring of absolute CD4 counts provides important information about determining the effectiveness of therapy, as well as the response to therapy.

Based upon the demands, the following design criteria was established for using the present invention to detect and enumerate CD4 cells in HIV patients:

1. Enumeration should be possible from 100 to 2500 CD4$^+$ T-cells/µl blood, but most critically in the 100-500 range. A count greater than 500 cells/□l is irrelevant. Also less than 200 cells/µl is the real critical level upon which clinical entry for therapy is advocated (see WHO treatment in resource poor settings). These latest guidelines stratify CD4 very simply and use hemoglobin (Hb) to clinically stratify patients.
2. Number of false positives (monocytes, other cells) below 10%. This is especially important where monocytes may be high e.g. co-infection with TB. TB is regarded as an AIDS defining illness below CD4 of 200/uL, and in the experience in South Africa cases, most of the CD4 counts are in the less than 200-400 range.
3. Cost price of hardware $1000 or less.

4. Maximum cost per test (including chemicals, antibodies etc.) $1 or lower. Flow cytometry using generic reagents costs less than $1-2 per test.
5. Minimal amount of laboratory handling required. This is an essential point for application in a resource-poor setting.
6. Use of disposables (cuvetes etc.) to avoid cleaning steps and for safety reasons. This does not mean that disposable systems only should be developed. In a very resource-poor setting, disposables may be beyond the reach, and a cleanable chamber might then be better. To prevent that "all" (disposables and blood) goes in the general garbage or down the drain, it may be a good idea to include a simple sterilizing system for disposables.
7. The overall system should be rugged and portable; have low power consumption (is battery-operated) and have an automatic data registration.

The invention described herein meets the criteria above. The invention uses a CCD camera to image samples. Object detection algorithms are performed on the captured image to count the number of target entities present in a sample.

The prior art contains many computer-assisted microscopes. U.S. Pat. No. 5,018,209 teaches a computer driven microscope in which the user manually selects positive events while looking at an image. Obviously, this does not have a high enough throughput to be an effective analyzer, especially in remote settings.

In U.S. Pat. No. 5,287,272, an automated cytological specimen classification system and method is described. This system relies on a complicated neural network to process images of cells based on morphology. While very effective for classifying objects in images, it requires a large amount of computational resources. Furthermore, human input and subsequent analysis is still necessary. Other devices, such as those described in U.S. Pat. Nos. 5,073,857 and 5,077,806, use window sub-image pixel counting algorithms for image analysis by using predetermined thresholds.

Another set of instruments in the prior art is designed as bench top analyzers. In U.S. Pat. No. 5,073,857, pap smears are analyzed by a computer controlled microscope and camera and computer driven image analysis. In U.S. Pat. No. 6,221,607, an automated microscope is described for analyzing in situ hybridization events in a biological specimen.

The devices in the aforementioned prior art are designed to image slides. None are capable of detecting and enumerating a target population within a biological specimen as defined herein. Furthermore, none appear to be portable or high throughput devices. These instruments are designed to rely on a desktop computer to control the microscope and camera, and to perform image analysis algorithms. The present invention overcomes many of the difficulties that lie in the prior art.

SUMMARY OF THE INVENTION

This invention (sometimes referred to herein by its project name, "EasyCount") describes compact electronic optical instruments, analytical methods, image acquisition, and data reduction algorithms for the detection and enumeration of magnetically labeled target cells or particles. Using whole blood as an example, blood cells are fluorescently labeled using one or more target specific fluorescent dyes, such as a DNA staining dye. The cells of interest or target cells in the blood sample are labeled by incubation with monoclonal antibodies conjugated to ferromagnetic particles. The sample is then placed into an appropriate optical detection chamber or cuvet, which in turn is placed into a magnetic field gradient that selectively causes the magnetically labeled cells to move towards the upper observation surface of the chamber. The target cells are collected and immobilized substantially uniformly on the optically transparent surface of the chamber. A segment of this surface and the labeled target cells thereon are illuminated by means of one or more LED (light emitting diodes). Subsequently, the light emitted by individual target cells is captured by a CCD (charge coupled device). Novel image acquisition methods, processing methods, and algorithms, specifically devised for this system as disclosed herein, are used to count the number of captured light-emitting cells. The data output is then related to the target cells per microliter of the sample in the chamber, and ultimately to the original specimen.

One embodiment of the present invention is magnetic manipulation of immunomagnetically labeled cells from a whole blood sample towards the upper glass observation surface of a sample chamber of a defined height. The system counts the number of cells present on the observation surface of a defined area. Since the height of the chamber and area of the observation region are known, the volume from which the cells are extracted can be determined and the number of cells present at the observation surface can be directly converted to the absolute number of cells in the sample.

Briefly, one of the assay method embodiments may be performed as follows: A sample from which one would like to investigate if and how many cells of a specific type are present is acquired. A fluorescent probe that labels all cells or all cells containing nucleic acid in the sample is added to the sample. Immunomagnetic particles labeled with a bioentity that discriminates this cell type from other cells in the sample are added to the sample. Cell labeling can take place in the cuvet or chamber used for analysis, or is transferred to such cuvet or chamber after sufficient time is allowed to permit cell labeling. The cuvet or chamber is placed between two wedge-shaped magnets that are designed such that all magnetically labeled cells move to the upper observation surface. The fluorescent label is chosen such that it is excited by an LED and the fluorescence emitted by the cells at the viewing surface is sufficient that the individual cells can be identified in the image captured by a CCD camera. The algorithms applied to the image identify and enumerate each of the objects or cells. Preferably the algorithm is programmed onto an embedded processor in the CCD camera. Finally, the cell counts per microliter of sample are displayed on a LCD.

The cells are counted based on their fluorescence intensity difference with the background. As excitation light source, LEDs are used which emission maximum of 470 nm that match the absorption spectrum of the fluorescent label. The emitted fluorescence is imaged onto a CCD camera. Image analysis routines, hard coded inside the system determine the number of cells present, and then the number of cells per unit volume. The development of the algorithms for image acquisition and data reduction required considerable laborious experimentation and optimization. This resulted in the present invention configuration that exhibits the excellent performance characteristics as described herein, notably an unexpectedly high S/N.

One particularly advantageous aspect of the present invention is its utility both as a research tool in cell biology and as a clinical tool in the diagnosis of diverse cellular, fungal and viral pathologies including but not limited to HIV and cancer. Further advantages provided by this invention are the functional simplicity in design, ruggedness, compactness, AC or DC power options, and substantially lower purchase and operating costs relative to conventional commercial devices with comparable performance characteristics. The features and improvements of the devices of this invention, exemplified as compact clinical cell cytometers, make them particularly useful for operation in primitive laboratories or under field conditions prevalent in resource-poor countries.

It is to be understood and appreciated that these discoveries, in accordance with the invention, are only illustrative of the many additional potential applications of the apparatus, methods and algorithms that may be envisioned by one of ordinary skill in the art, and thus are not in any way intended to be limiting of the scope of the invention. Accordingly, other objects and advantages of the invention will be apparent to those skilled in the art from the following detailed description, together with the appended claims.

DETAILED DESCRIPTION OF THE PREFERRED EMBODIMENTS

The technical terminology with reference to biological, clinical, electronic, mathematical and statistical expressions used herein conform to conventionally accepted definitions.

The terms "sample" or "specimen" are interchangeably used herein and refer to biological material obtained from tissue, spinal fluid, bone marrow, blood, or other sources. A sample can also include viruses, bacteria, or other pathogens. A typical example of a biological specimen would be blood drawn from a subject. As utilized herein the term "cells" refers to animal or plant cells, cellular bacteria, fungi, which are identifiable separately or in aggregates. For example, cells can be human red blood cells (RBC) and white blood cell (WBC) populations, cancer, or other abnormal cells. The terms "target" or "target population" refers herein to biological entities of interest that may be present in a biological specimen that is being analyzed. A typical example of members of a target population would be CD4 positive cells in a blood sample. Conversely, the terms "non-target" or "non-target population" as used herein refer to entities present in a biological specimen, are not the subject of the analysis.

System Design

Figure 1:
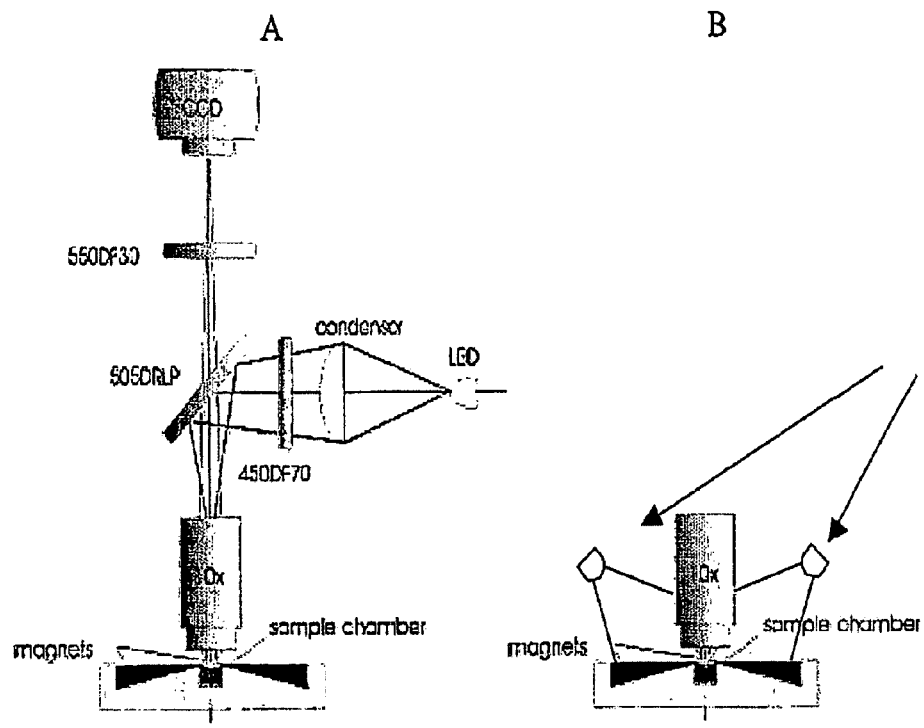
FIG. 1: Schematic representations of optical and illumination arrangements. In (A), light from an LED is focused on the sample through a condenser, a set of filters and a 10× objective. An image of the fluorescence of the cells is projected on and captured by a CCD camera. In (B), the light of two LED's is directly projected onto the sample.

The different components of the apparatus (sometimes referred to herein by its project name, "EasyCount") are shown in FIG. 1. The imaging part of the apparatus is based on an epi-illumination fluorescence microscope. The surface of the sample chamber is illuminated by a light emitting diode with a central wavelength of 470 nm (NSPB500S, Nichia Corp., Japan). The light emitted from the fluor-labeled cells at the inner surface of the chamber is collected by an objective and focused onto a CCD camera (EDC2000-N, Electrim Corp., Princeton, N.J.). This results in an image of 652×494 pixels, corresponding to a sample area of 0.55 $mm^2$, in which the cells appear as bright spots against a dark background.

Immunomagnetic Labeling

The term "specific binding pair" as used herein refers to molecules that have binding affinity for each other to the substantial exclusion of other molecules or entities. Examples of specific binding pairs include antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions. The phrase "to the substantial exclusion of" refers to the specificity of the binding reaction between the biospecific ligand or biospecific reagent and its corresponding target determinant. Biospecific ligands and reagents have specific binding activity with relatively high affinity for their target determinant, yet may also exhibit a low level of non-specific binding with substantially less affinity to other sample components.

The term "determinant", when used in reference to any of the foregoing target bioentities, refers broadly to chemical mosaics present on macromolecular antigens that often induce a heterophilic immune response. Therefore, determinants may be specifically bound by a "biospecific ligand" or a "biospecific reagent," and refer to that portion of the target bioentity involved in, and responsible for, selective binding to a specific binding substance (such as a ligand or reagent), the presence of which is required for selective binding to occur. In fundamental terms, determinants are molecular contact regions on target bioentities that to are recognized by agents, ligands and/or reagents having binding affinity therefore, in specific binding pair reactions.

The term "detectably label" is used to herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The terms "magnetically responsive" and "magnetically labeled" are used interchangeably herein, and refer to entities that have magnetic particles bound thereto. For example, these magnetic labels may bind to the surface of cells present in a biological specimen, or may bind to intracellular entities. In most of the embodiments described herein, the magnetic particles bind specifically to members of the desired target population, to the substantial exclusion of non-target entities. The term "magnetic manipulation" refers to placing the biological specimen in a magnetic field gradient with the intent to separate magnetically labeled entities from non-magnetically labeled entities. Magnetic manipulation may also occur when a magnetic field gradient is generated around the biological specimen, such as with an electromagnet.

To select and separate the target cells of interest, for example, from a whole blood sample, they are immunomagnetically labeled with a target specific antibody conjugated to magnetic particles, ferrofluids or superparamagnetic particles, as disclosed in U.S. Pat. Nos. 5,579,531 and 5,698,271 and U.S. application Ser. No. 10/208,939, each of which are incorporated by reference herein. The magnetic particles are typically about 180 nm in diameter and consist of a magnetic iron oxide core surrounded by a first polymeric layer to which streptavidin is conjugated. Target-specific antibodies can then be coupled to streptavidin by means of biotinylated antibodies. However, superparamagnetic particles made from other ferromagnetic materials, for example nickel, of similar or larger sizes of up to about 5 µm, can be similarly coated and used for magnetic labeling of target cells.

Finally alternative binders, such as lectins and boronate derivatives, recognizing glycosidic receptors on target cells may also be used in lieu of or in addition to antibodies on such magnetic capture particles.

For example, if the cells of interest are the total leukocyte population, a pan-leukocyte CD45 monoclonal antibody can be used that binds substantially specifically to all leukocyte populations in the blood sample. The cell labeling reaction can be conducted in test tubes or vials and an aliquot transferred to the sample chamber. Alternatively, the chamber itself can be used for incubations of specimen volumes of up to about 200 µl. The unbound non-magnetic materials are readily removable in the supernatants after magnetic separation. To enhance magnetic labeling efficiency of target cells one can use magnetic incubation or in-field incubation (PCT/US00/02034, which is incorporated by reference herein). To accomplish this, the sample is mixed with the magnetic ferrofluid in a test tube, and placed briefly inside a quadrupole high-gradient magnetic separator (HGMS) magnet (U.S. Pat. Nos. 5,186,827; 5,466,574; 5,641,072, incorporated by reference herein) after which it is removed from the magnet and remixed by vortexing. This step is repeated twice more. The quadrupole magnet delivers a radial magnetic gradient during the incubations, thus forcing the magnetic particles to move laterally as bead chains that sweep through the sample before accumulating at the wall surface. This multiple forced migration of magnetic particles increases the probability that the magnetic particles collide with or encounter the larger, substantially immobile, cells as compared to mere diffusional or Brownian collision of the magnetic particles and the target cells in the sample. Other magnetic configurations can be used that homogenously sweep through the sample.

Sample Chamber and Magnet Holder

As used herein, the term "observation surface" refers to an optically transparent wall of the sample chamber. When a biological specimen is to be visually analyzed, it is necessary for the target population to be adjacent to the observation surface. This allows the optical arrangement to clearly focus on the target population in order to provide an accurate analysis. Once the members of the target population have been magnetically labeled, they can be manipulated to the observation surface for visual analysis.

Figure 2:
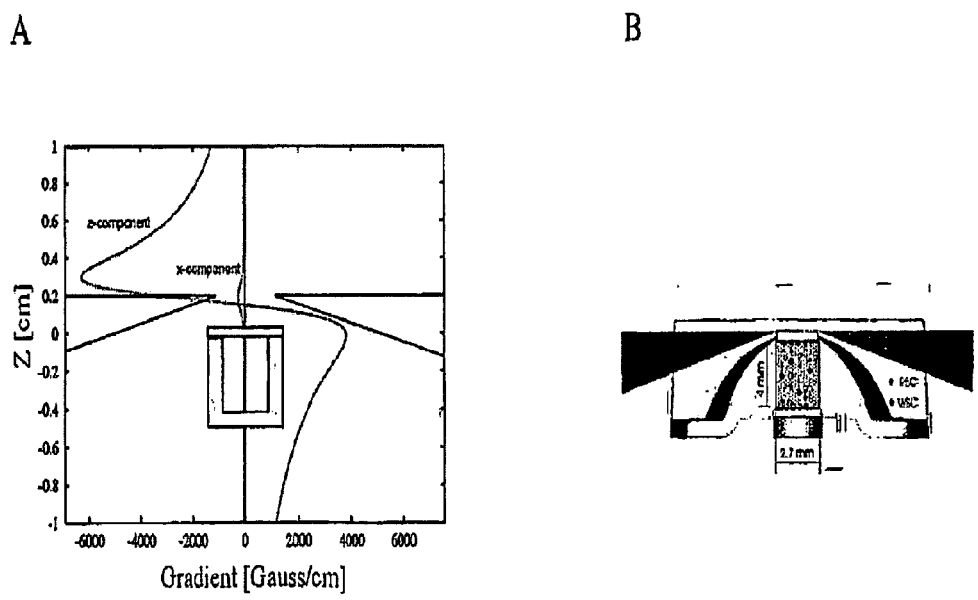
FIG. 2: (A) Magnetic gradient in the chamber in x- and z-direction. The x-component of the gradient is negligible. (B) Magnetically labeled white blood cells move upwards in the chamber, while unlabelled red blood cells move downwards.

The chamber and the magnetic yoke holder have been previously described (U.S. Pat. Nos. 5,985,153; 6,136,182; PCT/US02/04124, which are each incorporated by reference herein). The chamber consists of a molded body of inner dimensions 30×2.7×4 mm, length×width×height respectively. It has an optically transparent planar top surface of Pyrex glass (7740 Pyrex®; Corning International, Germany) that is sealable, if required, by W means of a removable plug cap. The sample chamber is shown (FIG. 2) oriented in the horizontal plane for probing with a vertical light beam. However, an alternative instrument design would accommodate an uncapped detection chamber or other suitable sample cuvet with the magnetic holder oriented vertically and the light beam oriented horizontally.

The magnetic chamber holder or yoke is designed such that the chamber is positioned 2 mm below the top of two magnetic pole pieces. The pole pieces are made of Neodymium Iron Boron alloy with an internal magnetization of 13,700 Gauss (Crumax Magnetics Inc, Elizabethtown, KT). The two pieces are mounted to form a 3 mm gap between their faces that are an angled 70° relative to the z-axis. This arrangement, depicted in FIGS. 2A and B, creates a magnetic gradient inside the chamber, which is pointing in the z-direction and has a negligible component in the x-direction. Therefore, the immunomagnetically-labeled cells and unbound ferrofluid particles move in the vertical direction to the upper surface. The imaged surface area correlates directly with the volume fraction underneath the imaged area (FIG. 2B). To obtain a representative and accurate number of cells per unit volume, it is important that the cells are uniformly distributed and immobilized over the viewing surface, which requires that the magnetic field conditions also are uniform over the full area of the glass surface.

A further improvement to the magnetic arrangement described above was to "spring load" the yoke assembly. This positions each sample cartridge into a repeatable location. Because of this, the specimens that are being analyzed are always in focus in the Z-axis as they are being imaged. This is extremely important for using the apparatus of the invention as a fast analyzer because independent focusing for each sample cartridge is no longer necessary. As the sample cartridges are manufactured with precision, the yoke assembly can position every sample to always be in focus.

Cell Dynamics in the Chamber

Since it is critical that all the cells in the sample are magnetically collected, it is important to know the time needed for the cells to arrive at the collection surface. The motion of an immunomagnetically-labeled cell, placed in the magnetic field, is dependent on the total force, F, exerted on the cell. This force is given by equation (1):

$$F_{total} = |m|\nabla B - M'g - 6\pi\eta v \quad (1)$$

The total force is the result of the magnetic force, the gravitational force and the viscous drag force. In this expression, $|m|$ is the magnetic moment magnitude of the cell and B is the magnetic induction. M' is the mass of the cell minus the mass of an equivalent volume of the serum in which the cell is suspended, g is the gravitational acceleration. The drag force is estimated by Stokes law, where $\eta$ is the viscosity of the medium, R is the cell radius and v is the velocity of the cell. The corresponding equation of motion in the y-direction for a cell is expressed by equation (2):

$$M'\frac{d^2y}{dt^2} + 6\pi\eta R\frac{dy}{dt} = |m|\nabla B_y - M'g \quad (2)$$

This second order differential equation can be solved for a cell with initial position y(0)=0 and initial velocity v(0)=0 as shown in (3):

$$y(t) = \frac{M'(|m|\nabla B_y - M'g)}{(6\pi\eta R)^2}\exp\left(-\frac{6\pi\eta R}{M'}t\right) + \frac{|m|\nabla B_y - M'g}{6\pi\eta R}t - \frac{M'(|m|\nabla B_y - M'g)}{(6\pi\eta R)^2} \quad (3)$$

The mass and radius of the cell and the viscosity of the medium are given values. The magnetic moment of the cell depends on the number of magnetic particles present on the cell membrane and thus dependent on the type of antibody used for magnetic labeling. For the calculation of the magnetic moment of the cells, a number of 100 magnetic particles per cell has been assumed. The magnetic induction is determined by the material and the geometry of the magnetic poles. The parameters used for the calculation of the forces acting on magnetically labeled cells and their motion in the magnetic field are the cell radius, R, of 4 the relative cell density, M', of 77 kg/m$^3$, the magnetic moment, m, of $9.32 \times 10^{-14}$ Am$^2$, the viscosity of blood plasma, η, of $1.8 \times 10^{-3}$ Pa and the magnetic gradient, ∇B, ranges from 250 Gauss/mm at the bottom to 400 Gauss/mm at the top of the chamber, and he lower value is used in the calculations. From equation (3), it can be calculated that a cell reaches its terminal velocity within a few microseconds. The velocity of a cell, $v_i$, in the chamber is therefore essentially constant. Obviously the velocity of a cell depends on the number of magnetic particles present on the cell surface. Since not all cells have the same epitope densities or number of antigens on their surfaces, there will be a distribution in the number of magnetic particles (and thus in velocities) of the cells. The velocities of a certain subpopulation of cells in the chamber can be represented by a normal distribution with mean velocity, $v_0$, and standard deviation σ. For a particular cell in the sample with initial position $y_{0,i}$ and velocity, $v_i$, the position in the chamber at time t can be written as (4):

$$y_i(t) = y_{0,i} + v_i t \tag{4}$$

The probability that the cell has reached the surface of the chamber is a function of time and the velocity of the cell. The latter is a stochastic parameter determined by a normal distribution (5):

$$P(v_i = v_0) = \frac{1}{\sigma \sqrt{\pi}} \exp\left(-\frac{(v_i - v_0)^2}{\sigma^2}\right) \tag{5}$$

At a certain time t, the probability that a cell i has reached the surface, is given by (6):

$$P_i(y_i = y_{surf}, y_{0,i}, t) = P_i\left(v_i \geq \frac{(y_{surf} - y_{0,i})}{t}, y_{0,i}, t\right) \tag{6}$$

$$= \frac{1}{\sigma \sqrt{\pi}} \int_{\frac{y_{surf} - y_{0,i}}{t}}^{\infty} \exp\left(-\frac{(v_i - v_0)^2}{\sigma^2}\right) dv$$

where $y_{surf}$ is the height of the chamber.

The distribution of cells in the sample can be assumed to be uniform, since the sample is exposed to the magnetic field immediately after insertion in the chamber. For a large population of cells, the expected number of cells (N) at the surface can be found by integration of the individual probabilities $P_i$ for all the cells in the chamber given by (7):

$$N(t) = \frac{N_0}{y_{surf}} \int_0^{y_{surf}} P_i(y_i = y_{surf}) dy_0 \tag{7}$$

$$= \frac{N_0}{y_{surf}} \sigma \sqrt{\pi} \int_0^{y_{surf}} \int_{\frac{y_{surf} - y_0}{t}}^{\infty} \exp\left(-\frac{(v - v_0)^2}{\sigma^2}\right) dv dy_0$$

where $N_0$ is the total number of cells present in the sample.

Figure 3:
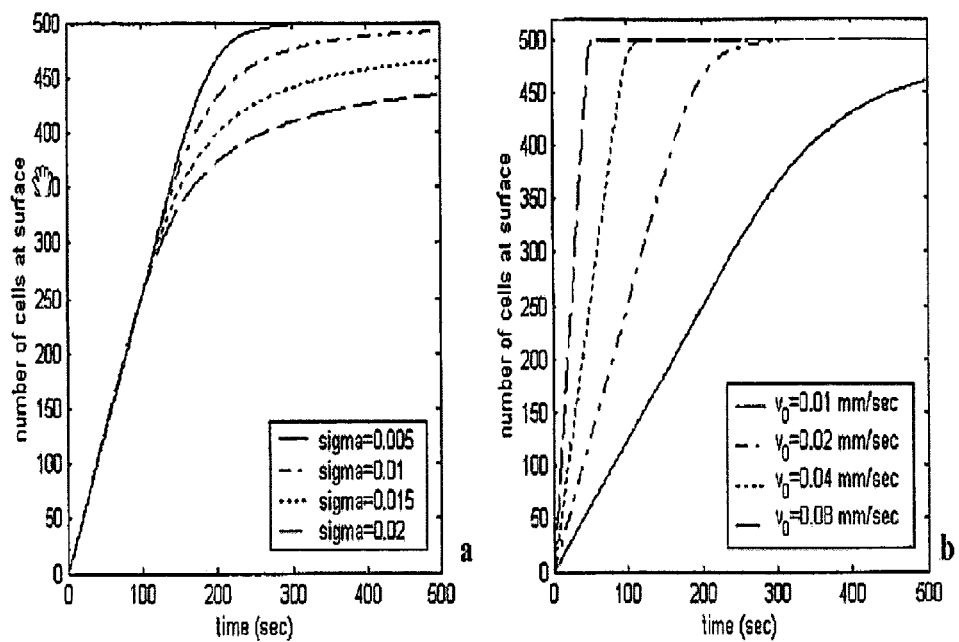
FIG. 3: The number of cells at the surface as a function of time for different cell velocity distributions. The initial slope of the curves represents the average cell velocity: a. Constant average cell velocity of 0.02 mm/sec, different values of σ. b. Different average cell velocities, for a constant σ of 0.02 mm/sec.

The expected number of cells, present at the surface as a function of time for a given cell population ($N_0$=500), is plotted in FIG. 3 wherein the different curves represent different velocity distributions. In FIG. 3a, the average cell velocity $v_0$ is constant, but different values for σ are used. In FIG. 3b, σ is kept constant and different average cell velocities are used. It should be observed that the initial slope of the curves corresponds to the average cell velocities in the chamber and, in fact, equation (8) follows from the solution of equation 7:

$$\frac{dN(t)}{dt} \approx \frac{N_0 v_0}{y_{surf}} \text{ for } t << \frac{y_{surf}}{v_0 + \sigma} \tag{8}$$

Other sample chamber designs are envisioned as well. For example, cartridges that are shallower may enable shorter separation times and may result in the analysis to be more selective of the target entities. It has been observed that non-target entities that become magnetically labeled, possibly through low level of antigen expression or through non-specific binding of the magnetic particles. However, these magnetically labeled non-target entities are much less magnetically responsive than the target entities that are specifically labeled. If the sample chamber were sized differently, these weaker magnetic entities would not travel to the sample chamber's observation surface, and would not contribute to "false positive" counts.

Sample Clarity

To avoid introducing air bubbles into the viewing or image capture area of the sample chamber, the magnet/chamber assembly was placed at about an 8° angle with respect to the horizontal plane. The influence on cell count was then evaluated at angles of about 0, 10, 20 and 90 degrees. No significant differences were observed at the various elevation angles.

Imaging System

Fluorescent Staining of Leukocytes

In order to make the nucleated cells detectable, the sample is stained with acridine orange (AO; Molecular Probes, Inc., Eugene, Oreg.), a vital dye that stains the nucleus of live cells as well as several constituents of the cytoplasm. Acridine orange has its absorption peak at 490 nm, and emits at 520 nm when bound to DNA. Other fluorescent dyes, such as Hoechst 33258, and Hoechst 33342 may be used. In general, any fluorescent dye that non-specifically stains cells, cytoplasm, cellular nucleic material, or the nucleus itself can be used. These dyes are referred to herein as "non-specific fluorescent dyes."

In general, illumination in fluorescence microscopy is achieved by mercury arc or quartz-halogen lamps. In some microscopy systems, more expensive lasers are used for illumination. However, recent advances in semiconductor technology have lead to the development of low-power, high-brightness light emitting diodes that can compete with incandescent light sources and lasers. The advantages of using LEDs as light source are that they are relatively compact and inexpensive, have a long lifetime, and are easily replaced. The spectral power distribution of a LED is fairly narrow, with half-bandwidths of about 20 to 50 nm, depending upon the substrate material. LEDs produce highly saturated, nearly monochromatic light and are ideal for constructing the compact and inexpensive cytometer devices of this invention.

Optics

The light from an LED is collected by a condenser lens with a focal distance of 27 mm, passes a 455DF70 band-pass filter (Omega Optical Inc., Brattleboro, Vt.), reflected by a 515DRLP dichroic mirror (Omega Optical) and focused at the back focal plane of a 10×, 0.25 NA objective (Nikon Corporation, Japan). This optical configuration results in a homogeneous illumination of the sample area. The light emitted from the fluorescent cells collected at the underside of the glass surface of the chamber is collected by the objective, after which it is filtered by a 550DF30 band-pass filter (Omega Optical) and focused onto a CCD camera (EDC2000-N, Electrim Corp, Princeton, N.J.). FIG. 1A shows the conventional epi-illumination mode. FIG. 1B shows a direct side illumination of the viewing surface with one or more LEDs in a "floodlight" arrangement, which provides sufficient excitation energy, and may be a simpler and less expensive illumination mode.

Camera

The CCD used in this set-up (EDC2000-N, Electrim Corp, Princeton, N.J.) has a dynamic range of 0-30,000 electrons. The r.m.s. (root mean square) of its readout noise, as given by the manufacturer, is 20 electrons. No data are supplied concerning dark current noise and amplifier noise. The image is retrieved from the camera by software and stored in a computer memory as 8-bit TIF images.

Image Processing and Analysis

Algorithms were developed to count the cells in the images obtained from the optical system. First, a model is presented to describe the cell images. Then, a method for spot detection in the images is introduced. Initially, these algorithms were performed on a desktop computer. An improved embodiment of the invention uses an imbedded processor within the CCD camera to analyze the images.

Image Model

Figure 4:
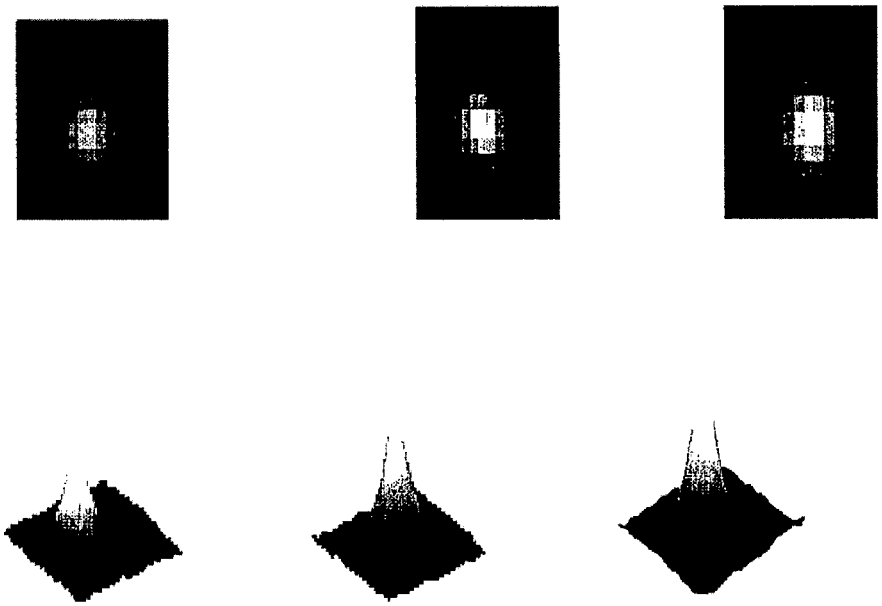
FIG. 4: Enlarged views of typical cell images and their intensity profiles. Based on these images, it is assumed that a cell can be modeled as a two dimensional Gaussian spot.

In this system, fluorescently labeled cells are located at random positions in the object plane. These cells are imaged as spots covering about 20-50 pixels in the image plane. Samples of cell images are presented in FIG. 4 A cell in the image can be modeled as a two-dimensional Gaussian with a width, $\sigma_p$ (equation (9)):

$$p(x, y) = \exp\left[\frac{-(x^2 + y^2)}{\sigma_p^2}\right] \quad (9)$$

The whole image f(x,y) with randomly distributed cells, including background and noise signals, is described by the following model:

$$f(x, y) = C_0(x, y) + \sum_i C_i p(x - x_i, y - y_i) + n(x, y) \quad (10)$$

where $C_i$ are the peak intensities of the cells. $C_0$ represents a slowly varying background level, which adds to the cells. This background signal is caused by free, unbound dye in the sample and can slowly fluctuate as a result of inhomogeneous illumination. A stochastic white noise component is modeled by the component n. Sources of noise include thermal and readout noise from the CCD camera. Based on this model we can define the signal-to-noise ratio (SNR) of cell i in the image:

$$SNR_i = \frac{C_i - \overline{C_0}}{\sigma_n} \quad (11)$$

where $\sigma_n$ is the standard deviation of the noise component n.

The image model contains parameters that can be estimated by analyzing existing cell images. For this purpose, 10 images were analyzed, which represent typical images obtained by the instrument. In Table 1, the image parameters for the 10 test images are shown. The images contain cells with different peak intensities. The mean SNR is the signal-to-noise ratio of the cell that has the average peak intensity in the image.

TABLE 1

Image parameters from 10 typical cell images.

| image | number of cells | mean $C_i$ | mean $C_0$ | mean $\sigma_n$ | mean SNR |
|---|---|---|---|---|---|
| 1 | 800 | 99 | 51 | 2.5 | 19.2 |
| 2 | 932 | 114 | 53 | 3.5 | 17.4 |
| 3 | 631 | 131 | 60 | 3 | 23.7 |
| 4 | 470 | 127 | 59 | 3.4 | 20.0 |
| 5 | 737 | 130 | 48 | 2.7 | 30.4 |
| 6 | 261 | 129 | 56 | 3.8 | 19.2 |
| 7 | 320 | 99 | 43 | 2.8 | 20.0 |
| 8 | 611 | 109 | 49 | 2.5 | 24.0 |
| 9 | 396 | 104 | 46 | 2.8 | 20.7 |
| 10 | 426 | 110 | 47 | 2.5 | 25.2 |
| Average | 558 | 115 | 51 | 3 | 22 |

Spot Detection

As shown in Table 1, the signal-to-noise ratios (about 22) of the images are surprisingly high and nearly constant over the full viewing area. This suggests that counting of the cells could be accomplished with high specificity. The optimized method consists of the application of a threshold to create a binary image in which cells get the value 1 (white), background and noise gets the value 0 (black) and the "white" spots in the image are counted. Obviously, the easiest way to count the cells is by using a preset threshold level, which is constant for all images. In practice, however, this method was found to be very dependent on the chosen threshold level. This is visualized in FIG. 5, which contains curves that are defined as threshold level curves. These curves show the number of counted objects in a cell image, plotted against the applied threshold level. Three threshold level curves of typical cell images are presented.

Figure 5:
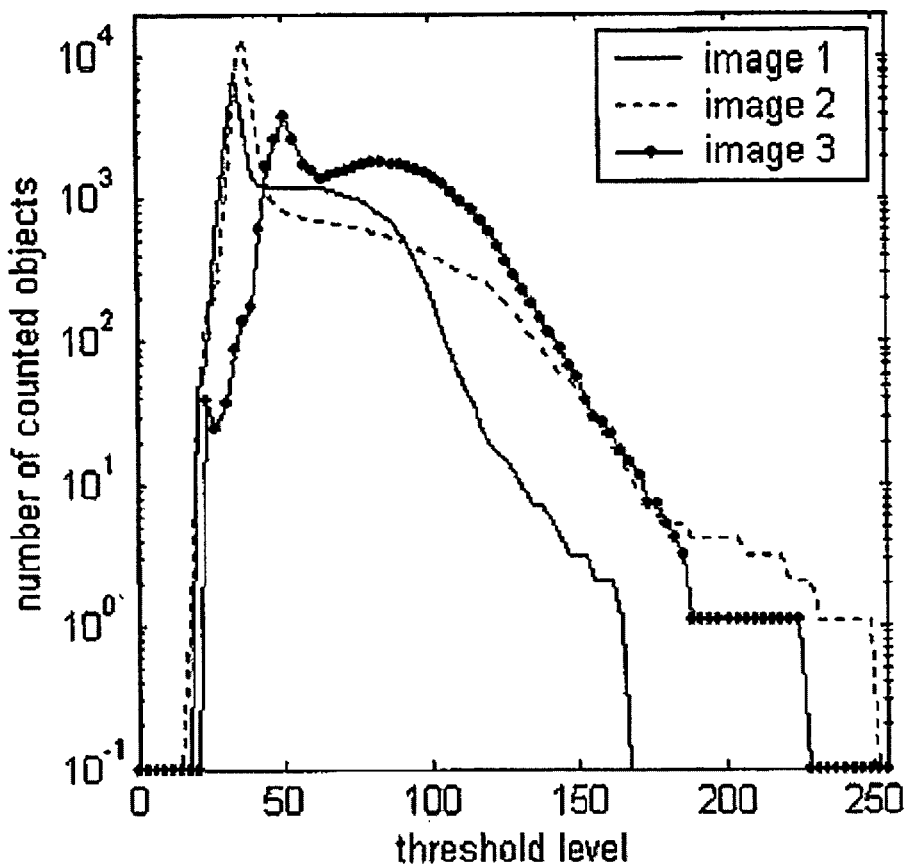
FIG. 5: Threshold level curves from three cell images obtained from the camera. The counted number of cells depends strongly on the chosen threshold level.

The curves in FIG. 5 show an initial increase in number of counted objects, where the threshold level is in the same range as the noise level of the image. This is because many of the noise pixels are assigned a 1. By increasing the threshold level further, a maximum is reached followed by a plateau. At this plateau, the noise is below threshold and all the cells are above threshold. This plateau thus corresponds to the actual number of cells. However, there is only a limited threshold level range where this plateau is relatively flat. This is the result of:

1. The intensity distribution of the cells. Dim fluorescent cells are just above noise level, while the brighter cells have large signal to noise ratios, resulting in a gradually decreasing number of counted cells at increasing threshold levels.
2. The presence of atypical artifacts such as bright (broken) pixels in the CCD camera.

The curve gradually decreases to zero as the threshold level increases to 255, the maximum pixel intensity of the image. FIG. 5 shows that only a narrow range is available where a preset level results in an accurate cell count. Furthermore, variations in background intensity would shift the curves horizontally, thus making the cell count very dependent on the chosen threshold level. Hence, a method is desired to make the counting more robust and less dependent on the chosen threshold level. Therefore, it was necessary to develop methods to elongate the plateau corresponding to the actual number of cells in FIG. 5 and the selected approach uses a matched filter algorithm to enhance the image prior to thresholding. This algorithm was extended with a non-linear Laplacian prefiltering step to further improve the cell counting process. It was also unexpected to observe that the following methods for image analysis were extremely successful at discriminating individual cells when they appeared close together in clusters.

Matched Filter Algorithm

The matched filter algorithm calculates the correlation between the observed image $f(x,y)$ and a suitably chosen template $h(x,y)$. The correlation is a measure of the similarity between the template and the image. The correlation between the image $f(x,y)$ and a $h(x,y)$ is calculated by convolving the two functions:

$$g(x, y) = \int_{-\infty}^{\infty}\int_{-\infty}^{\infty} f(x-\xi, y-\eta)h(\xi, \eta)d\xi d\eta \qquad (12)$$

The correlation should be maximized at the positions of the cells, where:

$$g(0, 0) = \int_{-\infty}^{\infty}\int_{-\infty}^{\infty} f(-\xi, -\eta)h(\xi, \eta)d\xi d\eta \qquad (13)$$

Good detection of cells means low probability of missing real cells and low probability of counting image points that are not real cells. This is expressed mathematically in terms of signal-to-noise ratio (SNR). Both probabilities are monotonically decreasing functions of the SNR. Hence, good detection requires maximizing SNR.

Ignoring for the moment the background, the SNR of spot i in the image is defined by to the quotient of the cell peak intensity and the standard deviation of the noise:

$$SNR_i = \frac{C_i}{\sigma_n} \qquad (14)$$

Convolving the image with a template $h(x,y)$ will change the SNR to:

$$SNR_i = \frac{C_i \int_{-\infty}^{\infty}\int_{-\infty}^{\infty} p(-x,-y)h(x,y)dxdy}{\sigma_n\sqrt{\int_{-\infty}^{\infty}\int_{-\infty}^{\infty} h^2(x,y)dxdy}} \qquad (15)$$

Figure 6:
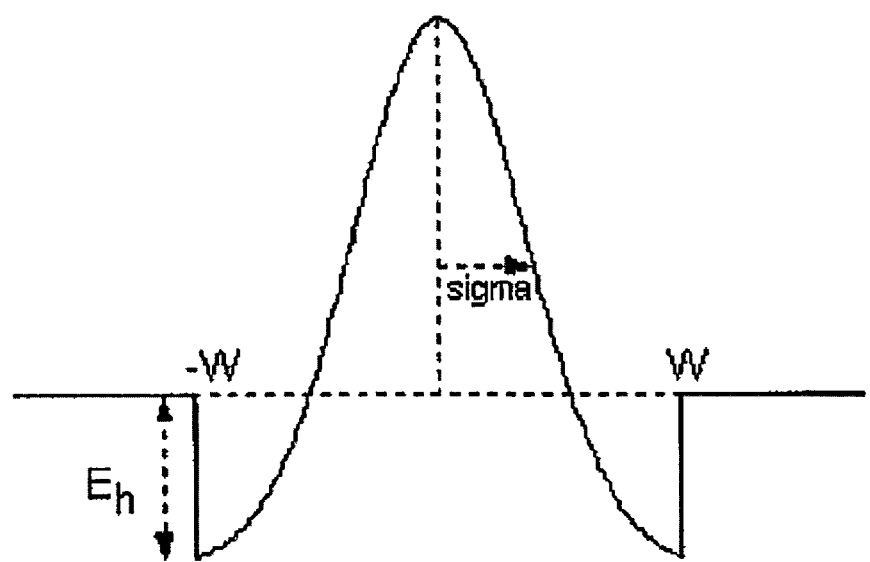
FIG. 6: Cross-section of the normalized template h(x,y). The template has zero average.
Figure 7:
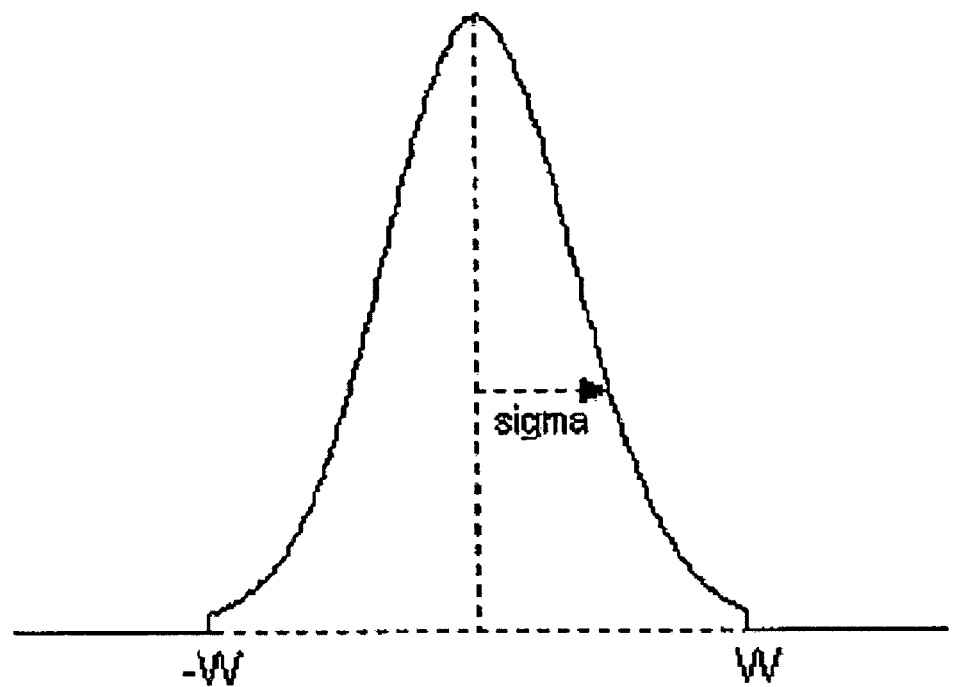
FIG. 7: Cross-section of the filter template $h(x,y|C_0(x,y)=0)$.

It can be shown by using the Schwartz inequality that the SNR is maximized when $h(x,y)=p(-x,-y)$. This means that the optimal template is simply the mirror image of the cell. This is why the method is usually referred to and defined as matched filtering or template matching. For our cell model, in the case without background signal, $C_0(x,y)$, $h(x,y)$ is symmetrical and therefore equal to $p(x,y)$:

$$h(x, y \mid c_0(x, y) = 0) = \frac{1}{\pi\sigma_p^2}\exp\left[-\frac{(x^2+y^2)}{\sigma_p^2}\right] \qquad (16)$$

$$(x, y) \in [-W, W]$$

where the volume under the Gaussian is normalized to unity. A cross-section of the template is presented in FIG. 6. In order to eliminate the influence of the slowly varying background level $C_0(x,y)$, DC removal is required. This can be achieved by normalizing the template $h(x,y)$ in such a way that it has a zero average value (see FIG. 7).

$$h(x, y) = h(x, y \mid c_0(x, y) = 0) - \qquad (17)$$
$$\frac{1}{4W^2}\int_{-W}^{W}\int_{-W}^{W} h(x, y \mid c_0(x, y) = 0)dxdy$$
$$= \frac{1}{\pi\sigma_p^2}\exp\left[-\frac{(x^2+y^2)}{\sigma_p^2}\right] - E_h$$

$$(x, y) \in [-W, W]$$

where $E_h$ is the average value of $h(x,y|C_0(x,y)=0)$. A constant signal yields a zero value after filtering, which can easily be shown by convolving $h(x,y)$ with a constant value.

Since $C_0(x,y)$ is the result of inhomogeneous illumination, DC removal can also be performed by determining the illumination profile and subtracting it from the image $f(x,y)$. However, the fact that DC removal can be accomplished simultaneously with the spatial filtering makes it the preferred method. $C_0(x,y)$ will be eliminated as long as the spatial frequencies of the background are sufficiently low, so that $C_0(x,y)$ is approximately constant within the area of the template.

Figure 8:
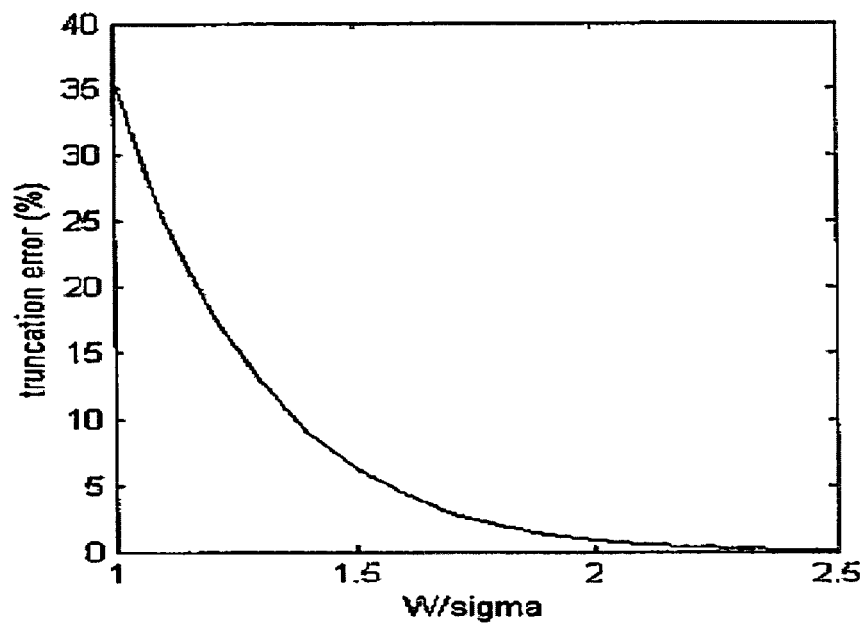
FIG. 8: Truncation error (%) introduced due to the use of infinite integrals and the finiteness of the filter template, as a function of the filter width. This error is negligible for larger values of W/σ since then the area under the Gaussian is relatively small for (x,y)>W.

The integrations of h and f are from $-W$ to $W$, because the template is finite. In the following calculations infinite integrals will be used to approximate the effect of the (finite) matched filter. This introduces a truncation error. However as long as $W>2\sigma_p$, which is the case as will be shown later, the error will be negligible because the area under the Gaussian at $|x|>W$ is relatively small. The error that is made by calculating infinite integrals while using a finite template is shown in FIG. 8.

Applying the matched filter $h(x,y)$ on the image $f(x,y)$ yields the filtered image $g(x,y)$:

$$g(x, y) = h(x, y) \otimes f(x, y) \qquad (18)$$
$$= \int_{-\infty}^{\infty}\int_{-\infty}^{\infty} [C_0 + C_i p(x-\xi, y-\eta) +$$
$$n(x-\xi, y-\eta)]h(\xi, \eta)d\xi d\eta$$

The signal part of $g(x,y)$ at the central position of cell i can be written as the dot product of f and h:

$$g_{s,i}(0,0)=h(x,y)\cdot f_{s,i}(x,y)=h(x,y|c_0(x,y)=0)\cdot f_{s,i}(x,y)-E_h\cdot f_{s,i}(x,y) \qquad (19)$$

Recognizing that $E_h \approx 1/4W^2$ for $W>2\sigma_p$, we can estimate the peak value of cell i after filtering:

$$g_{s,i}(0, 0) = \frac{C_0}{\pi\sigma_p^2}\int_{-W}^{W}\int_{-W}^{W}\exp\left[-\frac{\xi^2+\eta^2}{\sigma_p^2}\right]d\xi d\eta + \qquad (20)$$
$$\frac{C_1}{\pi\sigma_p^2}\int_{-W}^{W}\int_{-W}^{W}\exp\left[-2\frac{\xi^2+\eta^2}{\sigma_p^2}\right]d\xi d\eta -$$
$$C_0\int_{-W}^{W}\int_{-W}^{W} E_h d\xi d\eta - C_i\int_{-W}^{W}\int_{-W}^{W} E_h \exp\left[-\frac{\xi^2+\eta^2}{\sigma_p^2}\right]d\xi d\eta \approx$$

-continued $$\left(C_0 + \frac{C_i}{2}\right) - \left(C_0 + \frac{\pi\sigma_p^2}{4W^2}C_i\right) = C_i\left(\frac{1}{2} - \pi\sigma_p^2 E_h\right) \approx C_i\left(\frac{1}{2} - \frac{\pi\sigma_p^2}{4W^2}\right)$$

Figure 9:
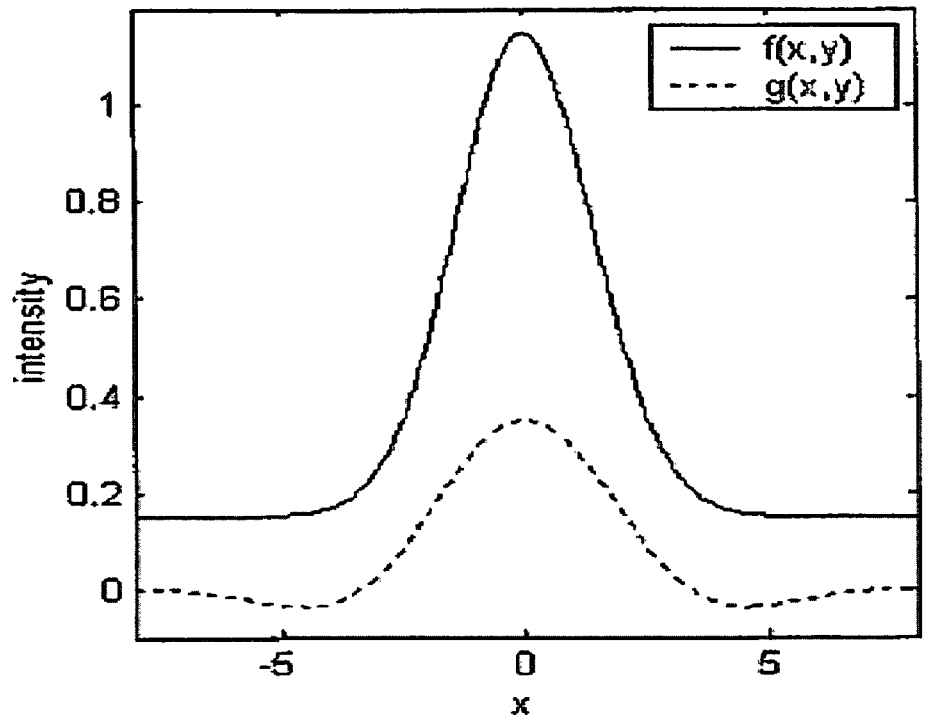
FIG. 9: Result of the convolution of the signal f(x,y) with the filter template h(x,y).

In FIG. 9 the result of the convolution is presented. In this case, $\sigma_p=2$ and $W=4.5$. The maximum value of g is approximately 0.34 times the maximum of f as is expected from the model. Negative side lobes appear as a result of the negative parts of the filter template. The constant background off is suppressed in g.

The noise is assumed stationary, signal-independent, white Gaussian noise with zero expectation value. Its standard deviation $\sigma_n$ after application of the filter can be written as:

$$\sigma_n \sqrt{\int_{-\infty}^{\infty}\int_{-\infty}^{\infty} h^2(\xi,\eta) d\xi d\eta} = \qquad (21)$$

$$\sigma_n \sqrt{\int_{-W}^{W}\int_{-W}^{W} \left[\frac{1}{\sigma_p^4 \pi^2}\exp\left(-2\frac{(\xi^2+\eta^2)}{\sigma_p^2}\right) - \frac{2E_h}{\pi\sigma_p^2}\exp\left(-\frac{(\xi^2+\eta^2)}{\sigma_p^2}\right) + E_h^2\right] d\xi d\eta} \approx$$

$$\sigma_n \sqrt{\left(\frac{1}{2\pi\sigma_p^2} - \frac{1}{4W^2}\right)}.$$

Figure 10:
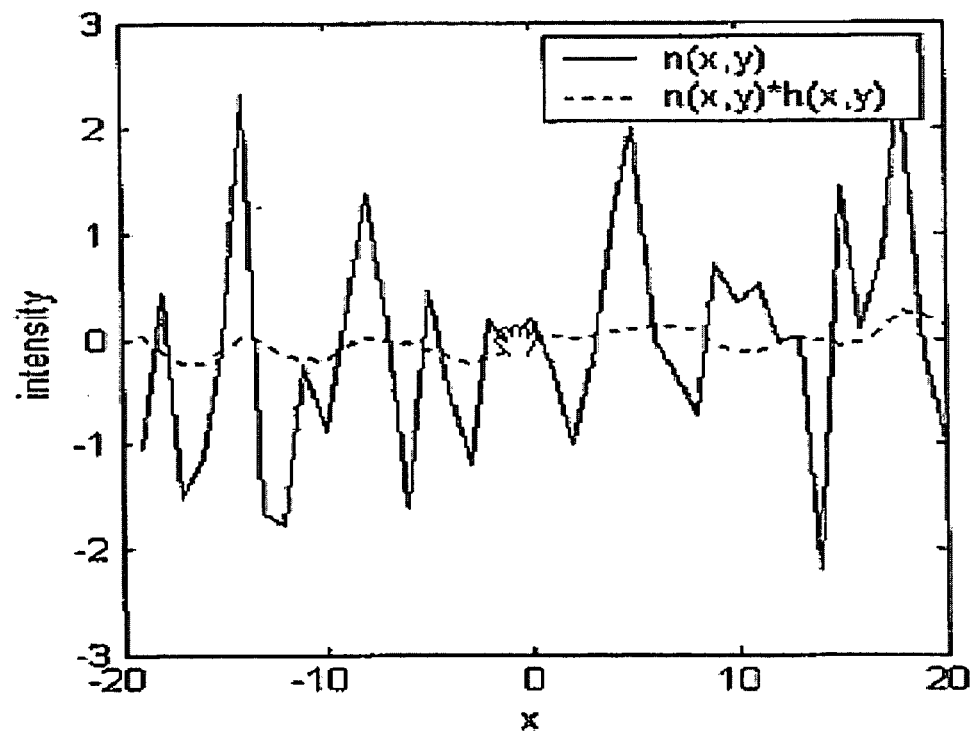
FIG. 10: The effect of the filter on Gaussian white noise. The filter suppresses the noise significantly.

The filter suppresses the high frequency component of the noise, thereby reducing $\sigma_n$. This is shown in FIG. 10 where Gaussian white noise is simulated before and after filtering. The standard deviation after filtering is $0.17\sigma_n$, in accordance to the model.

Hence, the SNR for cell i is now:

$$SNR_i = \frac{C_i\left(\frac{1}{2} - \frac{\pi\sigma_p^2}{4W^2}\right)}{\sigma_n\sqrt{\left(\frac{1}{2\pi\sigma_p^2} - \frac{1}{4W^2}\right)}} \qquad (22)$$

for $W>2\sigma_p$. Before filtering, $SNR_i=C_i/\sigma_n$ and thus the gain in SNR is:

$$A = \frac{SNR_i}{SNR_0} = \frac{\left(\frac{1}{2} - \frac{\pi\sigma_p^2}{4W^2}\right)}{\sqrt{\left(\frac{1}{2\pi\sigma_p^2} - \frac{1}{4W^2}\right)}} \qquad (23)$$

In the case of $\sigma_p=2$ and $W=4.5$, $A=2.1$, the gain in SNR is proportional to the width of the Gaussian, $\sigma_p$. It was observed that more noise tends to be filtered out when the width of the Gaussian increases. Filtering the image with a matched filter thus was found to enhance the signal-to-noise ratio. Additionally, the filter enhanced the detection because objects that do not match the template, like isolated bright pixels, are effectively suppressed.

Algorithm Parameters

Although the cells in the sample may be shaped and sized differently, all the cells in the cell image are of similar shape and are approximately of equal size. This is due to the magnification factor of the optical system, and the resultant influence of the point spread function. Since the approximate width $\sigma_p$ of the cells in the image is known, it can be directly used in the matched filter algorithm. It has been shown in the previous section that the filter performs best if it exactly matches the cell sizes. By visual inspection of several cells in the cell images, an average value of $\sigma_p=2$ has been determined. The final parameter left to optimize is the width of the template window, W. The contribution of pixels at the border of the template will have little effect, if $W>2\sigma_p$, since they are close to zero. When a small template is used, less noise and artifacts will be filtered out. Empirically, $W=4.5$ was found optimal for cell detection. This results in a 9×9 pixel template. Since $W>2\sigma_p$, the approximation condition of the previous section is satisfied.

Figure 11:
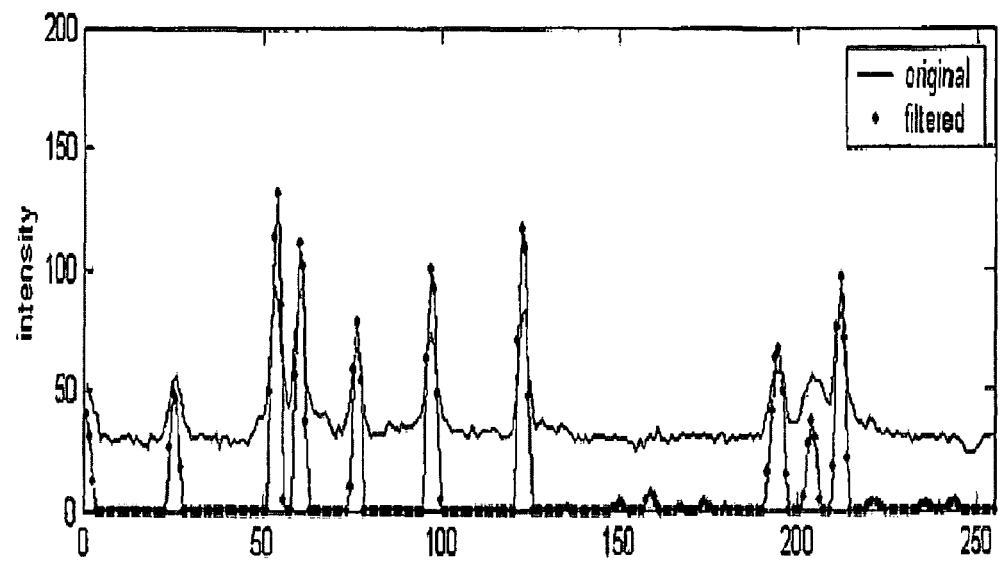
FIG. 11: Line trace from a typical cell image before and after filtering. The constant background level is suppressed and the cells are enhanced. Negative values are set to zero in the image.

FIG. 11 is a line trace from the original and the filtered version of a typical cell image. The effect of the matched filter for $W=4.5$ and $\sigma_p=2$ is shown. Notice that negative values are set to zero in FIG. 11.

Thresholding

The filtered image is now ready for thresholding, a necessary step, since object counting can only be performed in binary images. The following operation is applied on g(x,y):

$$g_{TH} = \begin{cases} 1 & g \geq t_0 \\ 0 & g < t_0 \end{cases} \quad 0 < t_0 < 255 \qquad (24)$$

which should separate the cells from the background and the noise. It is clear that the choice of $t_0$ is crucial in the cell counting process. Too small $t_0$ will introduce objects not corresponding to real cells, whereas a too high $t_0$ results in an underestimated or incorrect cell count.

Performance of the Algorithm

Figure 12:
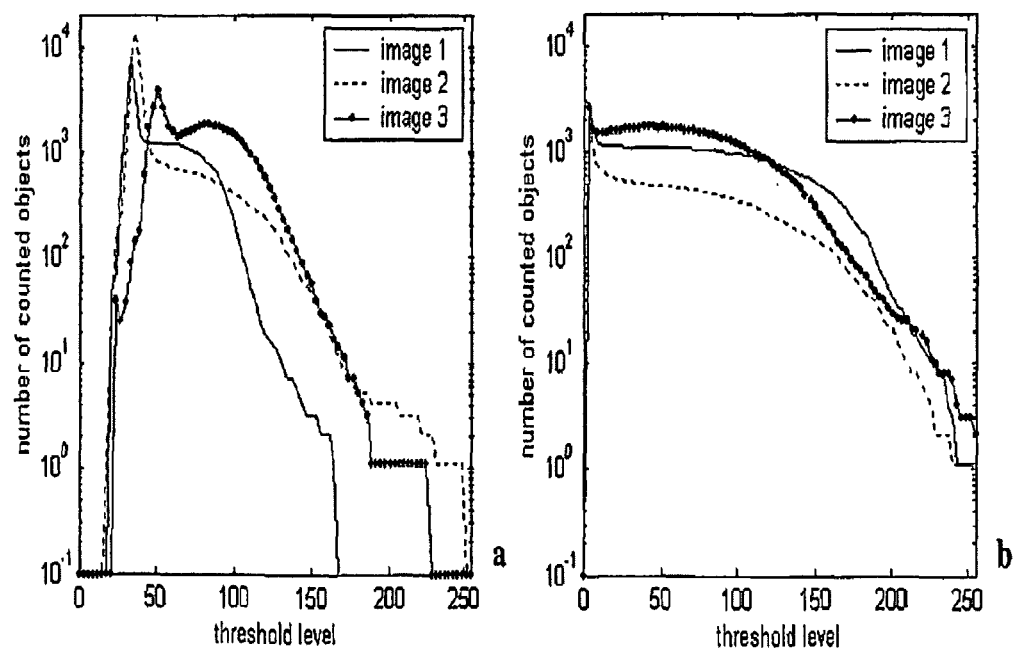
FIG. 12: Threshold level curves of three typical cell images. (a). Before filtering. The number of counted cells is strongly dependent on the chosen threshold level. (b). After filtering. The filter elongates the plateau of the threshold curves, making it easier to establish a predetermined threshold level for all images.

The effect of the template-matching algorithm is presented in FIG. 12. Again the counted number of objects in the image is plotted against the threshold level. In this case, a 9×9 pixel template was used with $\sigma_p=2$. The filter was applied on three different cell images. The figures show that the threshold range, for which there are a constant number of cells, is longer than in the unfiltered case. Also, the curves have shifted to the left as a result of the DC removal. This is an unexpected advantage since the plateau always has the same starting point regardless of the background level in the original image. This discovery makes it much easier to establish a predetermined threshold level that is applicable to all images.

Non-Linear Laplacian Prefiltering

The threshold curves presented in the previous section indicate that the counting process is made more robust by the matched filter alone, but still a gradual decrease of the curves is observed at higher threshold levels. This is due to the fact that there is a significant variance in cell intensities in the image. The linear matched filter does not alter this variance. One way to further improve the robustness of the algorithm is to apply a prefiltering step before the matched filtering, which reduces the variation in cell intensities. This was accomplished by a Laplacian filter, which strongly amplifies edges in the image. It has the following 5×5 kernel:

$$\begin{matrix} -1 & -1 & -1 & -1 & -1 \\ -1 & -1 & -1 & -1 & -1 \\ -1 & -1 & 24 & -1 & -1 \\ -1 & -1 & -1 & -1 & -1 \\ -1 & -1 & -1 & -1 & -1 \end{matrix} \qquad (25)$$

This filter will strongly enhance the cells in the image, and it increases the standard deviation of the noise. Indeed, the SNR decreases slightly by applying this filter. The reason why this filter is useful, however, is that the shape of the cells was found to remain more or less unaltered, and the amplification is so high that most cells clip onto the highest intensity level of the image. This implies that after applying the filter, the variance in intensities of the cells is reduced, i.e. all cells have approximately the same peak intensity.

Figure 13:
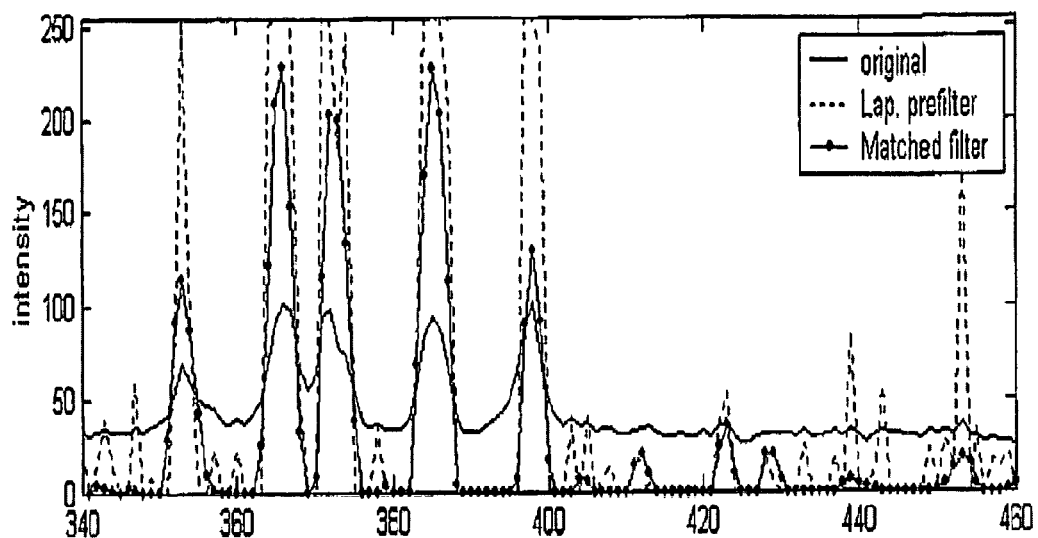
FIG. 13: Line trace from a typical cell image at different filtering steps. The Laplacian pre-filter strongly enhances the cells in the image and the matched filter suppresses the noise.

The matched filter was again applied, but this time to the prefiltered image. The matched filter extracts the cells from the slightly increased noise level, because it only amplifies objects that 'match' the filter. The cells are matched to the filter, whereas the noise is largely of high frequency. This is observed in FIG. 13 where a line trace of the image at three different steps is presented. The fact that the peaks are clipped did not really affect the performance of the matched filter.

Figure 14:
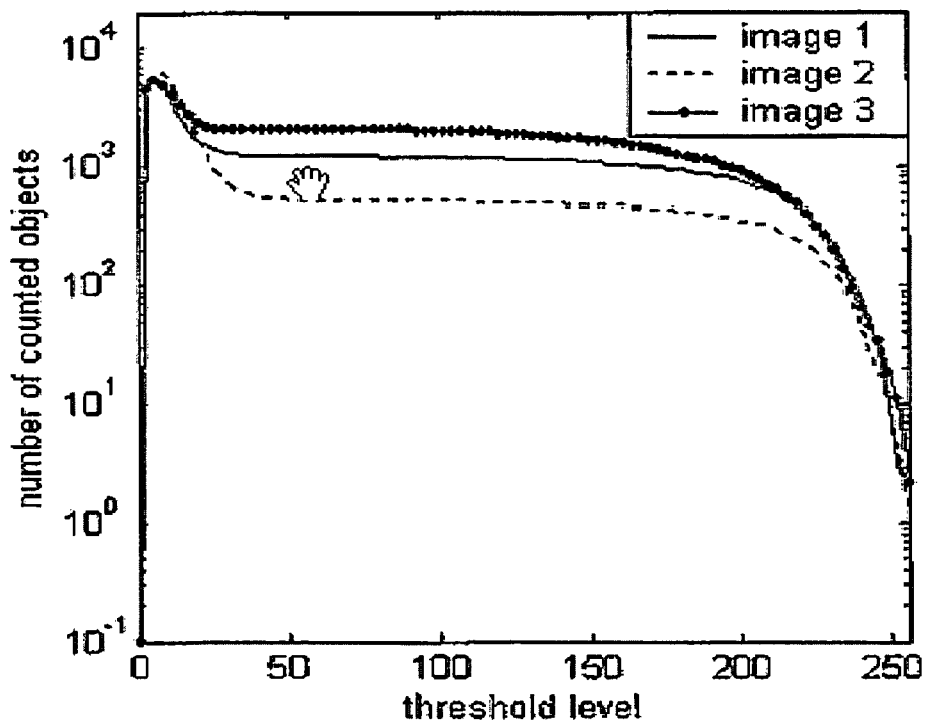
FIG. 14: Threshold level curve after application of the Laplacian pre-filter and the matched filter. The effect of the filters is a longer horizontal plateau, which makes the counting algorithm very robust.

FIG. 14 shows the threshold level curve after application of the Laplacian prefilter and the matched filter. The plateau is now longer, resulting from the cells having more or less the same intensities. Although the threshold level curves of only three images are shown, numerous images have been analyzed and the algorithm was surprisingly found to very robust in all cases.

Cell Counting

Counting objects in binary images is a well-known method, easily implemented with software. Therefore only a brief description of the counting algorithm will be given:
  1. The binary image is scanned, pixel-by-pixel (from top to bottom and left to right).
  2. When the scanning operator hits a pixel p with value 1, it is assigned a label. The first p found gets label 1.
  3. The operator examines the neighbors of p, which have already been encountered in the scan (i.e. the neighbors to the left of p, above p, and the two upper diagonal terms). Based on this information, the labeling of p occurs as follows:
      If all four neighbors are 0, assign a new label to p, else
      if only one neighbors has value 1, assign its label to p, else
      if one or more of the neighbors have value 1, assign one of the labels to p and make a note that the labels of the two neighbors are equivalent.

Figure 15:
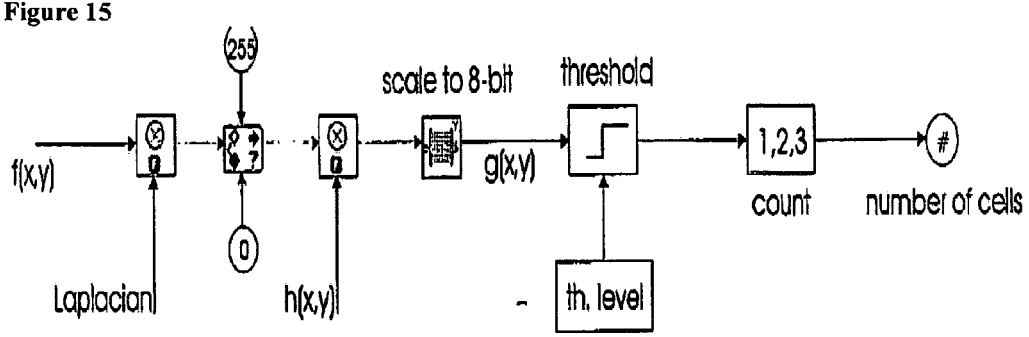
FIG. 15: Block diagram of the complete counting algorithm.
Figure 16:
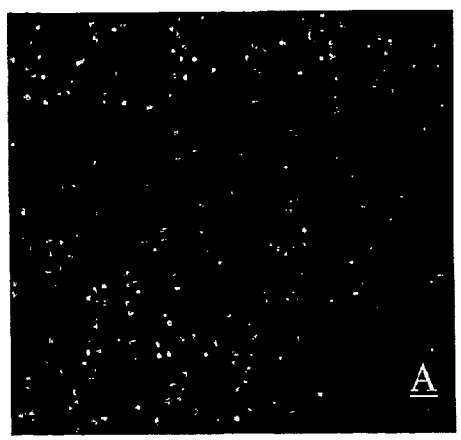
FIG. 16: Cell images at different stages of the image-processing algorithm. (a) Original cell image. (b) After the Laplacian prefilter. (c) After the matched filter. (d) After thresholding.
Figure 16:
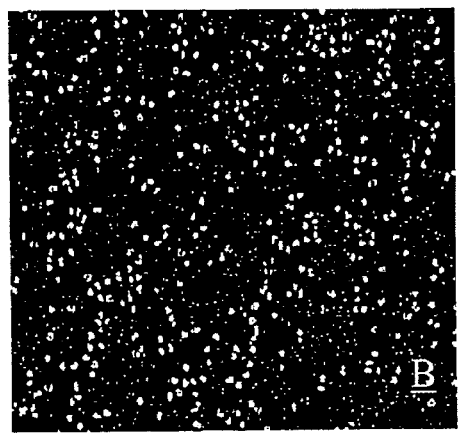
Figure 16:
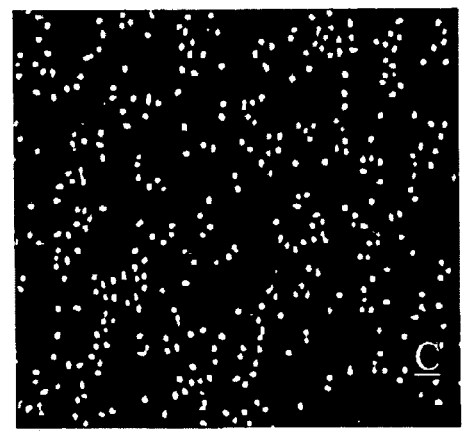
Figure 16:
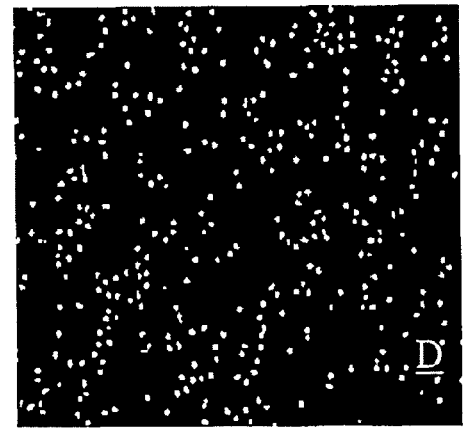

After completing a scan, a second pass is performed in which all equivalent labels are replaced with unique labels. Now, the number of labels corresponds to the number of regions to in the image. A schematic representation of the complete cell counting algorithm is presented in FIG. 15. After the first convolution with the Laplacian filter, the image values are restricted to values between 0 and 255 (8-bit format). Then the matched filter is applied. As a result, negative values and values above 255 were observed to occur. The image was then scaled back to 8-bit format to make it compatible with the original image and to enable is comparison of the original and the filtered images. FIG. 16 shows a typical unprocessed cell image, as well as the resulting dramatically improved images after different processing steps of the cell counting process. These imaging steps were surprising and unexpectedly highly effective in improving the image quality and resolution, which are essential in the algorithms of the present invention.

Simplified Template Matching Analysis

An alternative method for image analysis was developed and applied as follows. After the image has been acquired (CCD camera equipped with a Sony ICX085AL sensor) and stored in memory, the image size is 1300×1030 pixels. The optical arrangement allows each pixel to represent a 6.7×6.7 μm area. Then, dedicated image analysis routines are applied to find bright objects (cells) against a less bright background (white is 255, black is 0). This image analysis method relies on analyzing two regions, an inner rectangle (kernel) and a surrounding region. With the current magnification, the kernel is 7×7 pixels and the outer region is a 13×13 pixel rectangle surrounding the inner kernel rectangle.

First, the average brightness of the outer area, without including the kernel, is calculated. Next, the average brightness of the kernel is calculated. These averages are calculated for regions surrounding every pixel (center of the kernel identifies the pixel number). Next, the average of the inner kernel area is subtracted from the average of the outer area. If the difference is larger than the threshold value, an event has been found and is recorded. The analysis area is then shifted by one pixel, and the averages are calculated again. If the difference is larger than the threshold value a new event will be found.

Then, if the distance between the events is smaller than 7 pixels, the two events belong to the same object. The center of the object is found by determining the pixels where the difference between the average intensities of the kernel region and outer region is largest (best fit). Since the size of the surrounding region is 13×13 pixels, the minimum distance of the center of an object to the edge (horizontal and vertical) of the image is 13/2=7 pixels. Events present in the first 7 pixels are not detected.

This modified template matching method has a few advantages over the previous template matching methods. First, it requires less computational power and time. Because the typical template matching algorithm looks at full Gaussian profiles of object shapes, times for processing an image are on the order of an hour using a desktop workstation. However, when the simplified template matching algorithm (the inner rectangle and outer surrounding area) is used, the analysis time is a matter of minutes. Further, this analysis can be performed on a processor that is internal to the CCD camera.

Another benefit to the simplified template matching algorithm is that pre-filtering is no longer necessary. The simplified method inherently removes background noise as it compares the kernel region to the surrounding region. The reduction in analysis time using the simplified method is also a result of not needing the pre-filtering step.

User Interface

In one embodiment, the data from the processed images is evaluated through conventional LabView user interfaces. Several other dedicated interfaces have been developed, each with its own application. One such interface allows the user to load an image, adjust filter parameters, perform filtering and thresholding steps, obtain threshold curves and evaluate the number of cells in the image. Other user interfaces have been developed for other purposes, including processing of multiple images, obtaining image histograms and real-time capturing of images from the camera.

Initially, a desktop computer was required to process the images obtained from the camera. However, in applications such as cell counting in resource-poor settings, it is preferable to use a system, which does not depend on an AC power supply and extensive computer knowledge, and is easily performed. A possible component that may replace the computer currently used is a "smart camera," i.e., a digital camera with on-board integrated image processing hardware and software. Such a camera should be able to perform the image processing algorithms and output the results to, for instance, a palmtop computer or to a digital display. Such smart digital cameras are currently commercially available. They usually consist of a CCD and a digital signal processor allowing programming of image processing tasks. When such a camera replaces the computer, it is possible to use batteries as power supply for both the light source and the electronics. Also, the physical dimensions and the footprint of the apparatus is significantly reduced in the process, thereby enabling construction of the compact apparatus disclosed in this invention.

Illumination Efficiency

Light Source

The emission spectra of two different LEDs were measured using a monochromator (HR460, Jobin Yvon S A, France) in combination with a cooled CCD camera (Princeton Instruments Inc., Monmouth Junction, N.J.). The monochromator is equipped with a grating of 1200 lines/mm, which diffracts the LED light and projects it onto the CCD camera. Spectral lines of a neon lamp were used for calibration of the wavelength scale. Measurements were performed at driving currents of 1, 25, and 50 mA. The measured spectra show that LED 1 (NSPB500S, Nichia Corp, Japan) and LED 2 (110106, Marl International Ltd., Ulverston, UK) have almost the same spectral characteristics. This suggests that although the LEDs were obtained from different companies, both contain the similar diodes. Visual inspection by microscopy supports this speculation: both diodes are identical in structure and shape. A spectral blue-shift from 470 nm to 467 nm as well as a broadening of the spectra is observed at increasing driving currents. This can be attributed to band filling of localized states in the GaN material.

Illumination Model

Figure 17:
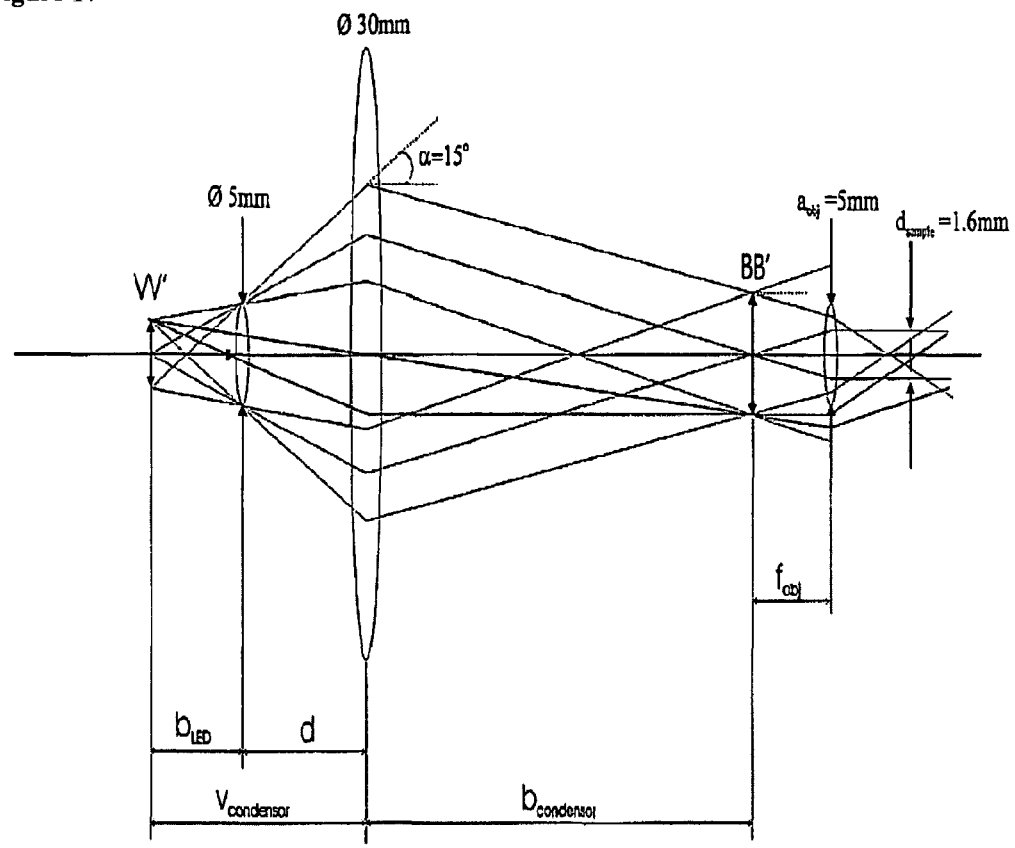
FIG. 17: Schematic representation of the optical system. The LED chip VV', as seen from the epoxy lens, is imaged at the back focal plane of a 10× objective, resulting in a parallel beam illumination of the sample plane.

A schematic representation of the illumination optical pathways is shown in FIG. 17. The epoxy lens in front of the diode collimates the light emitted by the diode chip. This results in a beam with an emission angle of 15°. A condenser lens (f=27 mm, Ø 30 mm) creates an image of the light-emitting area of the diode at the back focal plane of a 10× objective with an entrance pupil $a_{obj}$ of 5 mm, which results in a parallel beam illumination of the sample plane. The distance between the diode and the epoxy lens is less than the focal distance of this lens, resulting in a magnified virtual image of the diode in front of the epoxy lens. Since the diode and epoxy lens are fixed in the LED housing, one can treat the magnified and virtual image of the diode as the source object in the rest of this analysis. The object distance of the next lens, the condenser lens, can be written as:

$$v_{condenser} = b_{LED} + d \quad (26)$$

where d is the distance between the epoxy lens and the condenser lens. This results in the following expression for the image distance $b_{condenser}$:

$$b_{condenser} = \frac{(b_{LED} + d) f_{condensor}}{b_{LED} + d - f_{condensor}}. \quad (27)$$

It follows from equation 27 that $b_{condenser}$ will go to infinity if $b_{led} + d = f_{condenser}$ (=27 mm).

Figure 18:
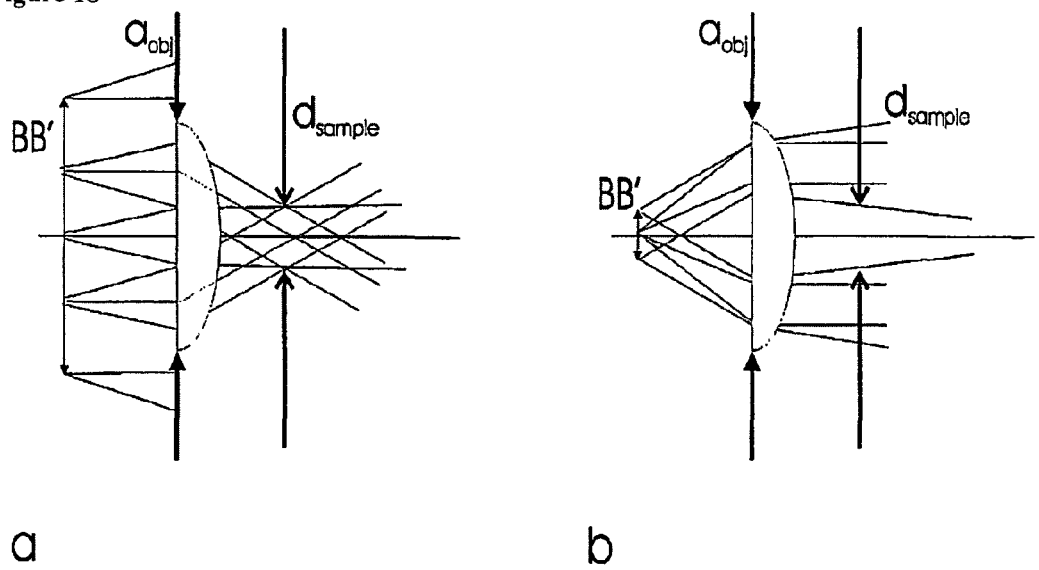
FIG. 18: Two limiting situations for the size of BB'. (a) BB' is much larger than the entrance pupil of the objective. (note: incident angles are small and light is lost outside the entrance pupil). (b) BB' is very small, resulting in a large beam diameter and light is lost at the sample plane. An optimal value for BB' is expected somewhere between these two limiting conditions.

By determining $b_{condenser}$ at different values for d, $b_{LED}$ was experimentally found to be 19 mm. The only parameter to be varied whilst conserving homogeneous illumination is BB', the size of the diode image in front of the objective. To maximize the light intensity at the sample plane, it is necessary to determine the optimal value for BB'. Two limiting situations can be distinguished:

1. BB'>>$a_{obj}$: The diode image is much larger than the entrance pupil of the objective and incident angles are small. This implies that all the light entering the objective is confined within the field of view. However, part of the light is actually lost in front of the objective, outside the entrance pupil (FIG. 18a).
2. BB'<<$a_{obj}$: The diode image is like a point source. Light enters the objective at large angles, but only light with small incident angles end up in the field of view. Part of the light is lost in the sample plane (FIG. 18b).

It is not easy to establish an analytical expression for the illumination efficiency, since we are dealing with an extended light source, resulting in off-axis rays. Also, different aperture stops are used at the epoxy lens, the objective entrance pupil and the field of view at the sample plane. These aperture stops block part of the light, but the actual amounts depends on the configuration of the optical components.

Figure 19:
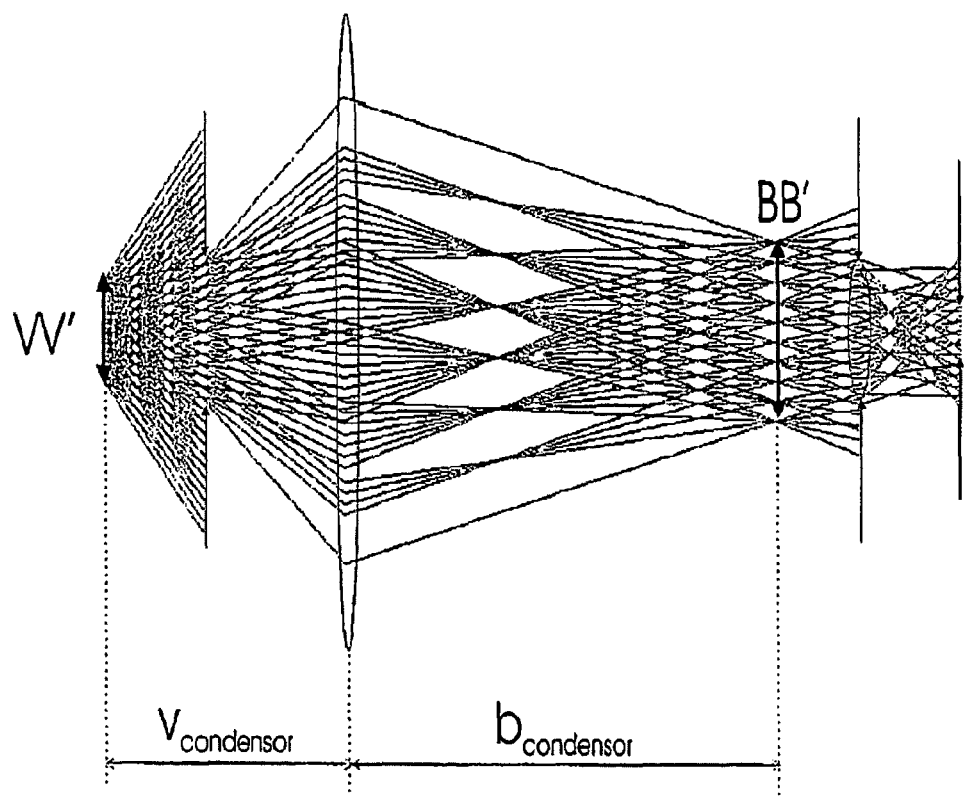
FIG. 19: Visualization of the geometric ray-tracing algorithm. The red rays are obstructed rays, the green rays remain within the field of view at the sample plane. The relative number of rays that pass through corresponds to the illumination efficiency (image not to scale).

Since an analytical solution is difficult to obtain, a basic geometric ray-tracing algorithm was developed to predict the efficiency of the illumination. The source was modeled as a circular disk with a diameter of 2 mm (equal to VV'). The source emits homogeneously over its area and in every direction. To calculate the efficiency, a large number of rays originating from the source were traced through the optical system, and at every aperture stop it was checked whether the rays were obstructed or could pass through. The efficiency was defined as the number of rays that reached the sample plane divided by the total amount of rays leaving the epoxy lens of the LED. A visualization of the algorithm is shown in FIG. 19 where both the obstructed rays and the rays reaching the sample plane are shown. It was observed in FIG. 19 that the maximum angle of the light rays from the LED is determined by the epoxy lens, and that some of the rays are blocked in front of the objective. Furthermore, some rays end up outside the field of view at the sample plane. The illumination efficiency was calculated for different sizes of BB'. To control BB', the object distance $v_{condenser}$ and the image distance $b_{condenser}$ were varied. There is indeed an optimal value for BB', where the illumination is the brightest and this optimum is found at BB'=4 mm.

Calibration Cartridge

Calibration sample chambers containing known amounts of synthetic fluorescent beads have been produced and shown to be detectable by the system's CCD. These control chambers have the beads embedded in a polymer matrix. By imaging these cartridges, the instrument can be tested to ensure each system (illumination, optics, detection, enumeration, and reporting) is functioning properly. Furthermore, these cartridges will be very useful for quality control and initial calibrations during instrument production.

A description of various experiments is given that were performed to optimize and characterize the system. Extensive experiments and measurements were carried out to determine the spectral characteristics of the light source, the optimal method of illumination and the performance of CCD cameras. Furthermore, the performance of the image analysis algorithms described in the previous section was tested and found to be highly effective. The experiments described in the following examples are used to illustrate the capabilities of the present invention. They are not intended to limit the scope or use.

EXAMPLE 1

System Characterization

To evaluate the theoretical predictions, the following experiment was done. A photodiode was placed in front of the objective, at the sample plane. A diaphragm restricted the illuminated area on the photodiode to a disk with a diameter of 1.6 mm. The LED and the condenser lens were placed in different configurations, so that an image of the diode chip was created at the back focal plane of the objective, and the size of this image was varied from almost a pin-point source to 25 mm.

Figure 20:
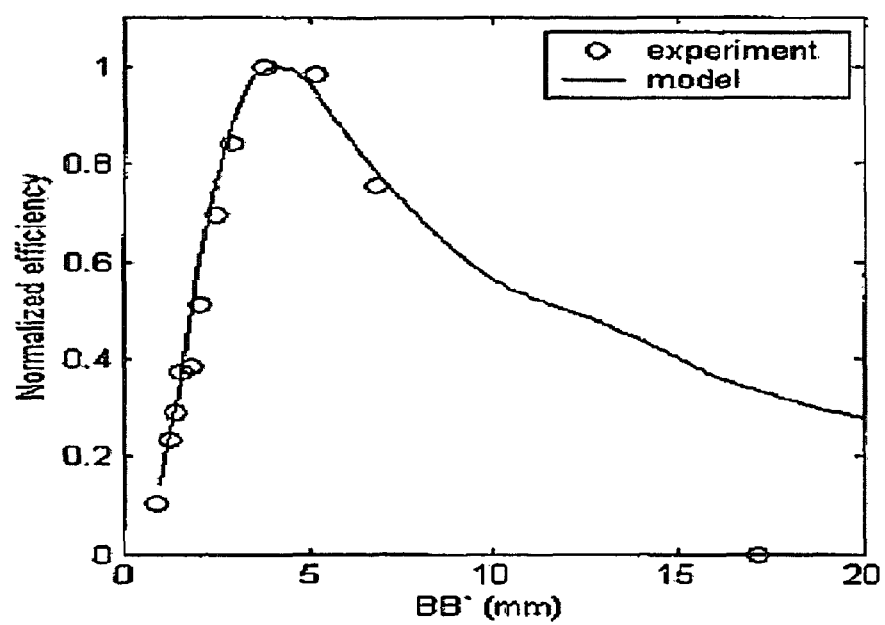
FIG. 20: Experimental data of the normalized illumination efficiency fitted to the data from the ray-tracing algorithm. The experimental values are in good agreement with the values predicted by the algorithm.

The result of the experiment is presented in FIG. 20 where the curve obtained from the ray-tracing algorithm is shown together with the experimental data. As was predicted by the algorithm, an optimal value was found for the size of the image at the back focal plane of the objective. The shape of the curve resembles the situation predicted by the algorithm, except for large values of BB', where the experiment shows an efficiency of almost zero. This may be the result of the fact that the real light source is inhomogeneous and square instead of homogeneous and circular. The results of both the model and the experiment agree both showing that the optimal value for BB' is 4 mm. This was realized using the following parameters, $v_{condenser}$=46 mm and $b_{condenser}$=83 mm. The physical dimensions of the set-up to allow these parameters, so they were chosen in order to obtain optimal illumination.

Magnification

The magnification of the optical system is determined by imaging a calibration grid. The spacing of the grid is 25 μm/line. The field of view is therefore 0.65 mm×0.85 mm and the image size is 494×652 pixels, hence a single pixel corresponds to 1.7 μm² in the sample plane. The total area of the sample plane that is contained by the image is 0.55 mm².

Measurement Volume

Free and unbound dye in the sample causes a background signal in the CCD camera. This signal is dependent on the sample volume that is illuminated by the LED and also was found to depend on the optical properties of the sample. To determine the illuminated volume for a sample of 10× dilution of whole blood, for example, acridine orange was added to a final concentration of 5 μM and the sample was placed in a wedge-shaped chamber. This chamber was imaged at different positions, and the average intensities of the resulting images were measured. The background signal was found to increase with depth to a depth of 4 to 5 mm. At larger chamber depths, the background signal remained constant. This indicates that the measurement depth is about 4 mm, which coincidentally is the same as the depth of the standard chambers that is normally used.

Camera

Figure 21:
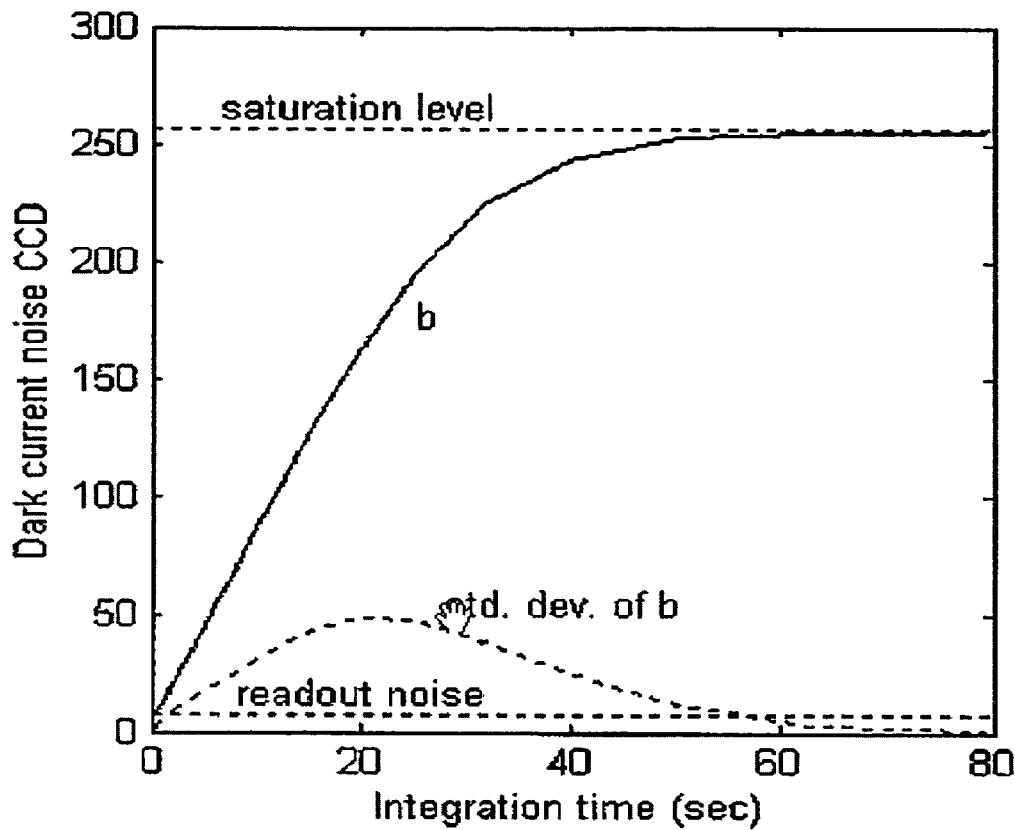
FIG. 21: Average value and standard deviation of the dark current noise from the camera. At longer integration times the camera gets saturated.

It is desirable to determine the relationship between the input signal of the camera (i.e. photons from the sample plane) and the output signal (intensity level in the 8-bit image). If this relationship is known, we can determine the fluorescence intensity of, for instance, cells in the sample based on the measured intensity of the pixels in the digital image. In case of a linear camera response, the intensity level of a pixel in the image can be described by:

$$I_{pixel}(P,t) = AP_{pixel}t + bt + \underline{n}(t) \qquad (28)$$

where A is the gain of the camera, $P_{pixel}$ is the radiant power over the pixel area, t is the integration time, b is the dark current, c is the readout noise and n is shot noise, a function of the integration time. The unit of pixel intensity is DN (digital number). The dark current and readout noise parameters are easily determined by covering the camera aperture and measuring the average output signal of all the pixels of the CCD. The relationship between b and t is presented in FIG. 21. The dark noise variance $\sigma_b$ is also shown in the figure. It is observed from FIG. 21 that the average dark current noise level increased linearly with the integration time, as is expected for thermal noise, and has an offset, due to the readout noise of the camera. From the figure we derive the parameters:

b=8.1 c=4.5

$$t<20 \text{ sec} \qquad (29)$$

At integration times longer than 20 sec, the camera was saturated by noise. The standard deviation of the dark current noise is expected to be a function of the square root of the integration time, since the distribution of thermal electrons is a Poisson process. However, the data in FIG. 21 unexpectedly showed a slightly different behavior, and the dependency on the integration time was found to be rather linear. The reason for this finding remains unclear, but may it be caused by other noise sources in the camera or electronics. The standard deviation decreases at t>20 sec, again due to saturation of the camera. For $\sigma_b$, the following expression is obtained:

$$\sigma_b(t) = 3.8t + 0.8$$

$$t<20 \text{ sec} \qquad (30)$$

Figure 22:
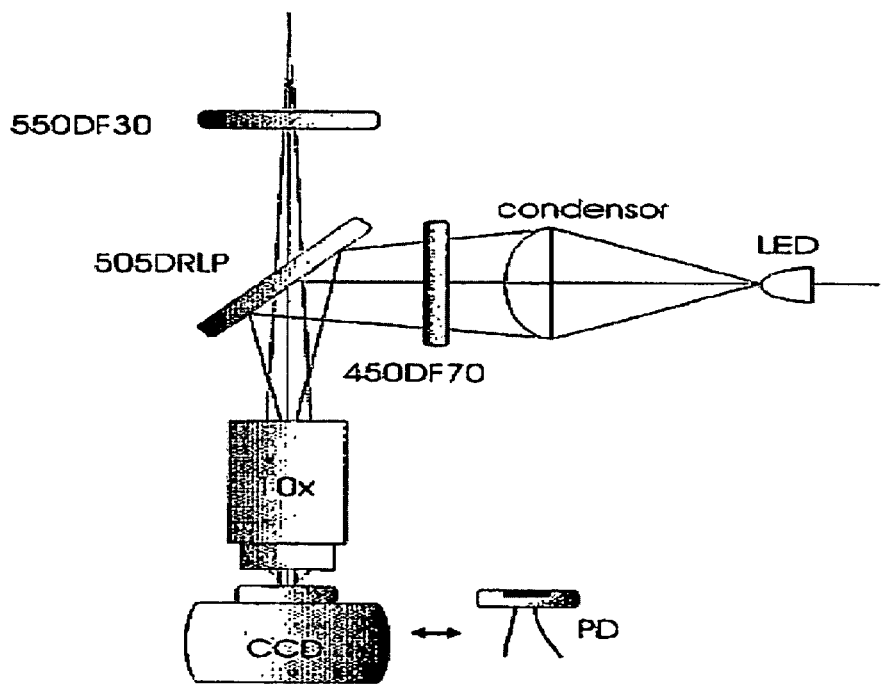
FIG. 22: To calibrate the output signal from the LED, the photodiode was placed in the sample plane and the radiant power was measured for different LED driving currents. To measure the camera response to the known LED signal, the CCD camera was placed in the sample plane and the average pixel intensity was measured.

To determine the gain parameter A, we needed to measure the camera response to a known input signal. If the input signal is controlled by either intensity or by exposure time, we could derive A by estimating the slope of the resulting straight-line curve. The standard light source of the set-up, a blue LED, was used to generate an input signal to the camera. To accomplish this, the CCD camera was placed in the sample plane directly in front of the objective (see FIG. 22). The radiant power was controlled by varying the driving current to the LED. The relationship between the driving current and the radiant power of the LED at the sample plane was calibrated first using a silicon photodiode with known responsivity that was placed directly in front of the objective. Once this relationship was established, the pixel intensity in the CCD image was measured as a function of the radiant power of the LED light. Grey filters with a known attenuation factor were used to attenuate the signal from the LED. This was necessary to prevent the camera from getting saturated. To confirm the assumption that the camera output signal increases linearly with the integration time, a dye solution (AO) was used as a sample and imaged at different integration times. The result was indeed a linear relationship.

The camera response can be written as:

$$I_{pixel} = (4.7 \times 10^{14} P_{pixel} + 8.1)t + 4.5 \qquad (31)$$

or $$P_{pixel} = 2.1 \times 10^{-15} \frac{I_{pixel} - 8.1t - 4.5}{t} \text{ [W]} \qquad (32)$$

Since the characteristics of the camera with respect to the sensitivity and noise are now defined, the parameters were used to determine the minimum radiant power that is required to yield a detectable signal in the image. The signal-to-noise ratio (SNR) for a single pixel in the image can be written as:

$$SNR = \frac{I_{signal} - I_{bg}}{\sqrt{I_{signal} + \sigma_{noise}^2}} = \frac{4.7 \times 10^{14} Pt - 8.1t - 4.5}{\sqrt{4.7 \times 10^{14} Pt + (3.8t + 0.8)^2}} \quad (33)$$

A single pixel in the image receives light from 1.7 μm² in the sample plane, so that the corresponding power density in the sample plane is:

$$M = \frac{P}{1.7 \times 10^{-12}} \ [W/m^2]. \quad (34)$$

We can write the relation between the signal-to-noise ratio and the power density as:

$$SNR = \frac{8 \times 10^2 Mt - 8.1t - 4.5}{\sqrt{8 \times 10^2 Mt + (3.8t + 0.8)^2}} \quad (35)$$

Figure 23:
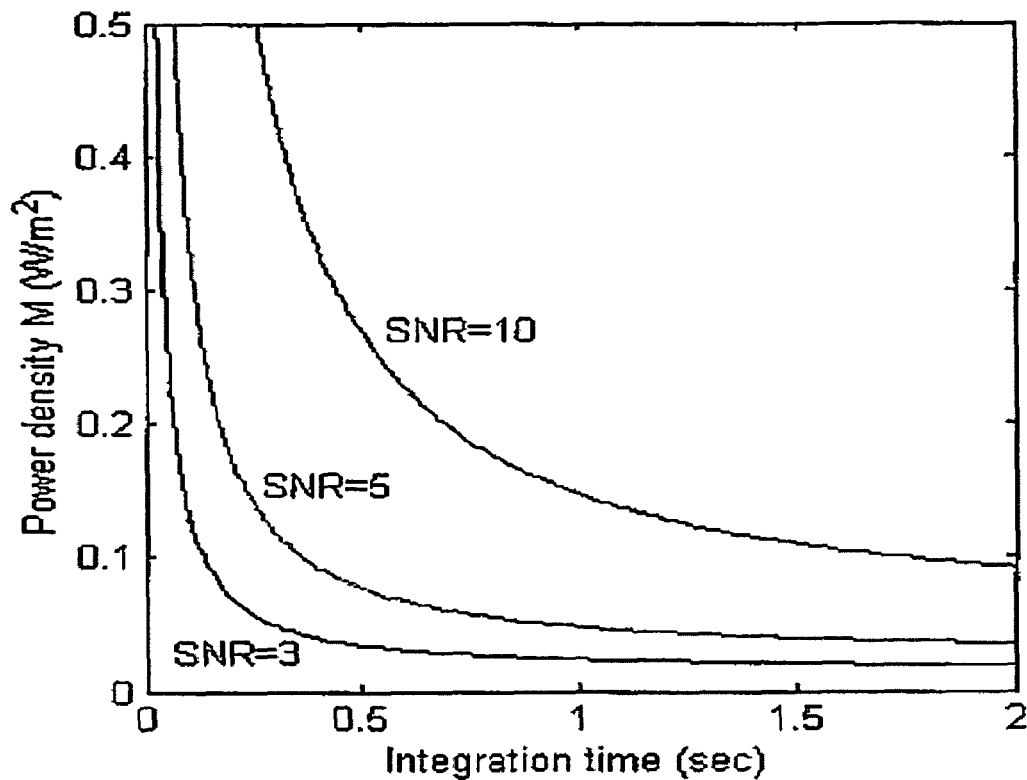
FIG. 23: Combinations of the integration time t and the power density M that result in a certain signal-to-noise ratio.

FIG. 23 shows the combinations of M and t required to yield signal-to-noise ratios of SNR=3, SNR=5 and SNR=10.

Image Analysis

It has been shown that the filters applied to the images result in a robust counting algorithm, which are not significantly dependent on the threshold level. To ensure that the algorithm performs well in all situations, a large number of images with different numbers of cells were analyzed. To further investigate the accuracy and stability of the image processing steps, simulated cell images were used. The simulated images resemble the real cell images obtained from the CCD camera, but their properties are known. Analysis of both the real and simulated images makes it possible to select the optimal threshold level.

Threshold Level

Figure 24:
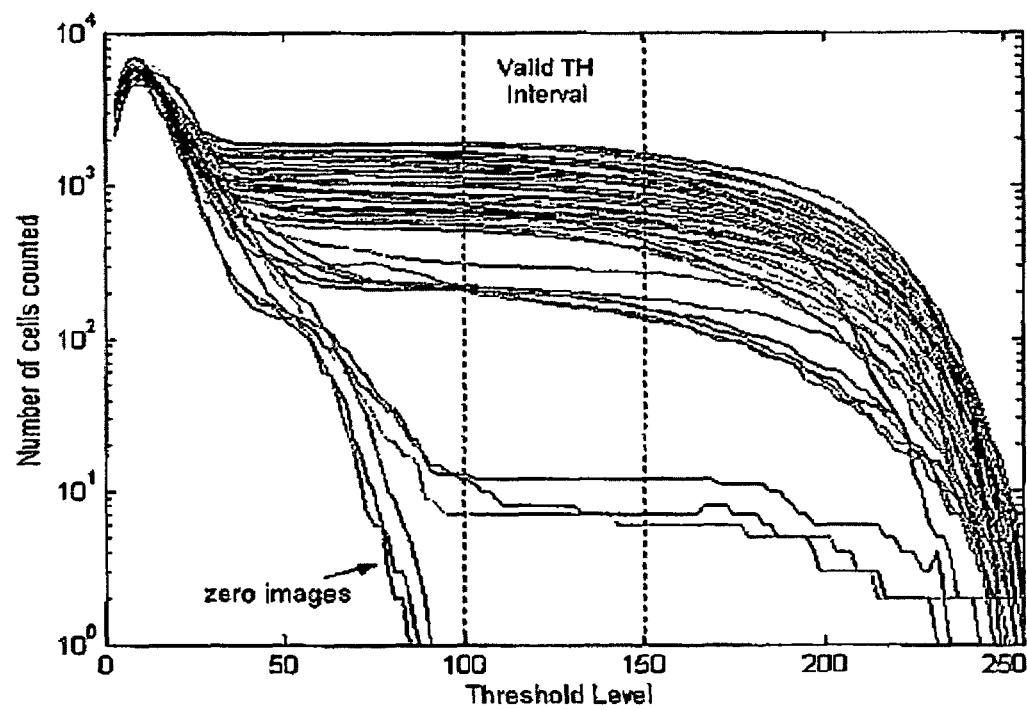
FIG. 24: Threshold level curves of 45 cell images, including 3 'zero' images. Based on these curves a valid threshold level interval between 100 and 150 was established.
Figure 25:
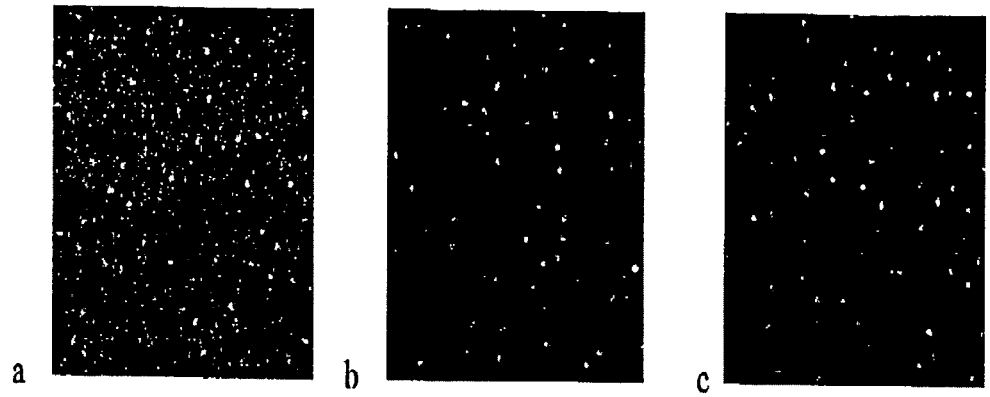
FIG. 25: Simulated cell images with different signal to noise ratios (SNR), which were used to investigate the effect of SNR ratios on the counting accuracy. (a) SNR=3 (b) SNR=10 and (c) SNR=20.
Figure 26:
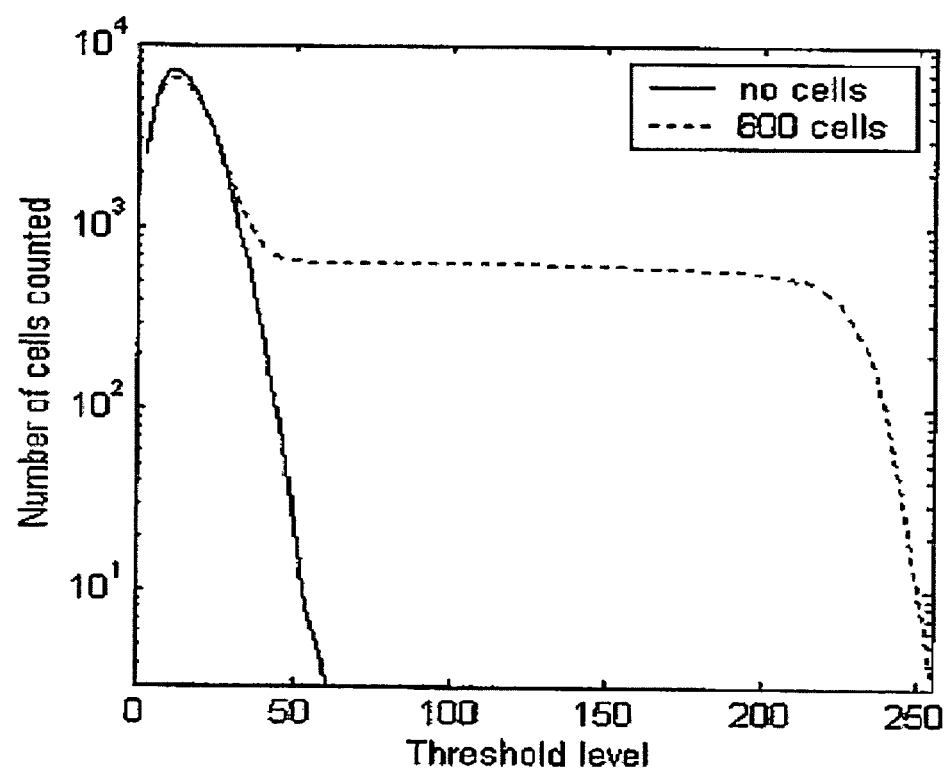
FIG. 26: Threshold level curves of two simulated images. Note the resemblance between these curves and the curves obtained from the real images in FIG. 24.

To determine the optimal threshold level, 45 cell images with cell numbers ranging from 7 cells/image to 1150 cells/image were analyzed and threshold curves were calculated. Three images without cells were also analyzed. The result is presented in FIG. 24. In the figure, the valid threshold level range is indicated. The lower limit is determined by the position where the zero images do not further contribute to the cell count, while the upper limit is determined by the shape of the threshold curves, because of their gradual decay. To control the signal-to-noise ratio in the images and to investigate the effect of the signal-to-noise ratio on the counting accuracy, simulated images were used. The simulated cell images consist of a known number of cells N with a normal intensity distribution with mean $I_0$ and standard deviation σ. The cells are modeled as two-dimensional Gaussians. The images also have a constant background level $C_0$, a noise component n and a number of bright isolated pixels similar the real cell images. A number of cell images were simulated with different signal-to-noise ratios, varying from 1 to 25. Several of the simulated images are presented in FIG. 25 (SNR=3, SNR=10, SNR=20). The image parameters for the simulated images were derived from the parameters of the real cell images. This resulted in de values: $I_0$=110, σ=20, $C_0$=50 and N=600. The simulated images were then analyzed by the image processing software. FIG. 26 shows the threshold curves for two simulated cell images: an image without cells and one with 600 cells. The signal-to-noise ratio was 20, similar to the real images. As can be observed in the figure, the shape of the threshold curves of the simulated images is similar to the shape of the real image curves in FIG. 24. The simulated images were analyzed to evaluate the performance of the counting algorithm. The detection error was defined as:

$$\text{Error} = \frac{|\text{Counted number of cells} - N|}{N} * 100\% \quad (36)$$

Figure 27:
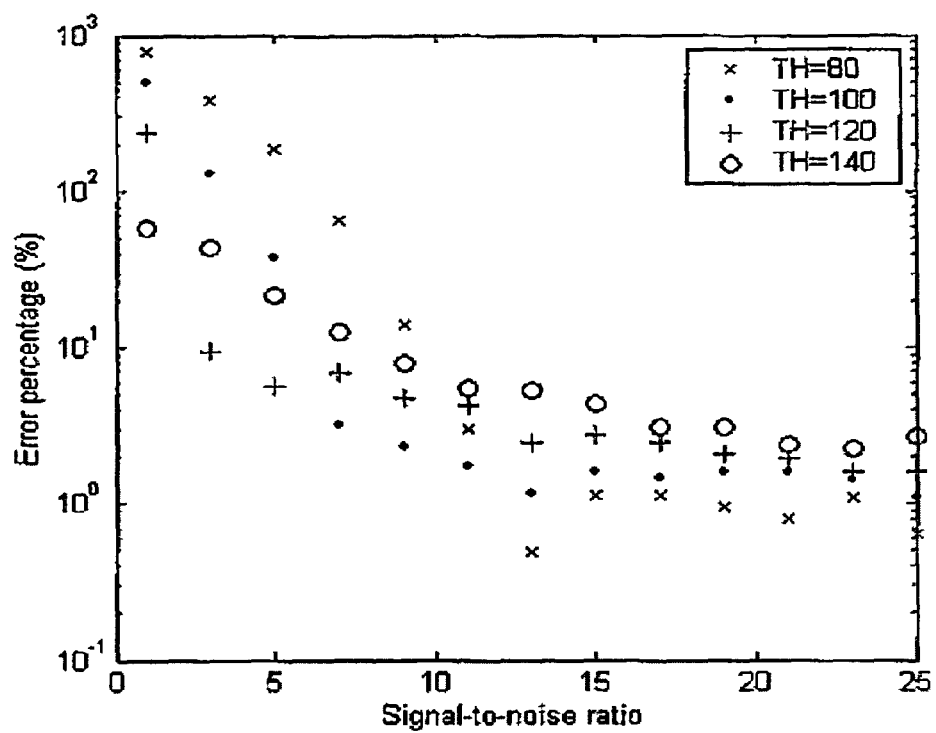
FIG. 27: Error percentage of cell counting as a function of the signal-to-noise ratio of the simulated images. At the average signal-to-noise ratio in the real cell images (SNR=20), the data show an error of approximately 2%.

FIG. 27 shows the results for four different threshold levels: 80, 100, 120 and 140. The error decreases with increasing signal-to-noise ratio. The signal-to-noise ratio in the real cell images is typically 20. These findings demonstrate that, based on these simulations, the error due to image processing inaccuracy is expected to be about 2%.

EXAMPLE 2

Total White Blood Cell Counting

Isolated white blood cells were spiked into a leukocyte-depleted red cell concentrate at known leukocyte concentrations, which ranged from 5 to 30,000 cells/μl. The samples were then processed according to the following total leukocyte selection protocol. To 100 μl of EDTA anti-coagulated whole blood in a 12×75 mm glass tube, 20 μl 100 μ/μl biotinylated CD45 monoclonal antibodies were added. After 30 minutes of incubation at room temperature, 10 μl of 0.4 mg/ml streptavidin-ferrofluid was added. Then, the sample was placed in and out of a HGMS magnetic quadrupole (QMS13, Immunicon® Corp., PA) three times (10 seconds each time). After standing for another 30 minutes, 5 μl of 3 mg/ml acridine orange was added and the sample was diluted to a final volume of 2 ml with Cell Buffer (Immunicon Corp, comprised of mainly phosphate buffered saline or PBS) and a 320 μl aliquot of the sample was then inserted into the sample chamber. The chamber was capped and immediately placed in the magnetic chamber holder. Three images were made of every sample.

In an alternative mode, the sample chamber would consist of an uncapped cuvet, bearing optically flat surfaces that can be oriented vertically rather than horizontally for illumination with a horizontal light beam.

Linearity

The number of cells per μl of blood can vary significantly between different persons, and in some diseases this number can decrease or increase dramatically. This means that in some applications, a range of at least three orders of magnitude can be expected. The performance of the system with respect to linearity over a wide range of leukocyte concentrations needed to be evaluated by measuring blood samples with known numbers of leukocytes.

Figure 28:
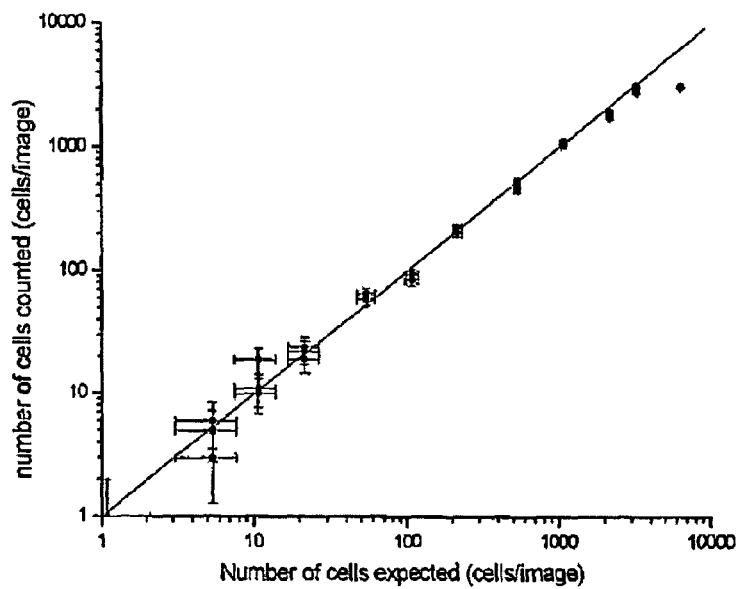
FIG. 28: Counted number of cells vs. expected number of cells. The system is linear up to about 1500 cells/image (slope=0.98, $R^2$=0.99). At higher cell densities the cell count is underestimated by the system. The error increases at lower cell densities due to the low sample size.

The result of an associated experiment is presented in FIG. 28. A slope of 0.90 ($R^2$=0.99) was observed. This low slope shows the result of including the three deviant measurements at the highest cell concentrations of about 1500 cells/image. If these high data points are disregarded, the slope of the line significantly increases to 0.98 ($R^2$=0.99). About 1500 cells/image can thus be regarded as the upper limit at which the system performs accurately. The error bars increase significantly at low numbers of cells per image thus setting the lower limit of the dynamic range of the system. The density of cells at the surface is based on the dilution of the blood sample. If the approximate concentration of cells in the sample is known, the dilution can be increased or decreased in order to yield an optimum surface cell density. However, since the dilution factor cannot be smaller than 1, the minimum number of cells/µl that can be counted with a statistical accuracy of <5% is about 180 cells/µl, unless more than one surface position is imaged.

Reproducibility

The reproducibility of a cell count corresponds to the variance in the number of cells counted when a sample is recounted repeatedly. The magnetic configuration is designed in such a way that along the centerline of the chamber, the cells on a surface segment surface originate from the fractional chamber volume below that surface segment. It is expected, however, that there may be some variation in cell densities along the lateral position of the chamber.

Figure 29:
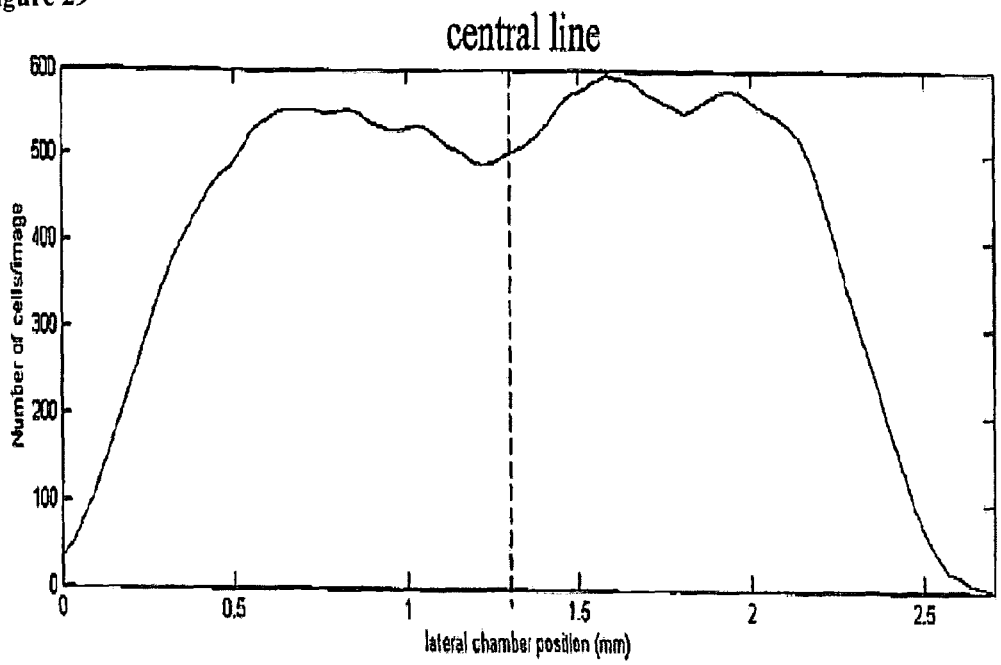
FIG. 29: Number of cells/image at different lateral positions of the chamber surface. At the edges of the surface the cell density decreases. The magnets are designed in such a way that halfway between the magnets the cell count is most accurate.

Additionally, there may also be variations when the sample is analyzed at different surface positions or segments or in different types of chambers. In an ideal system, these variations are subject to Poisson distribution statistics, and the variance will depend on the number of counted cells. Other factors may also contribute to variations in the cell counts. The distribution of cells in lateral positions was determined by taking four (partly overlapping) images at different lateral positions or segments and calculating the moving average of the number of cells. The result is presented in FIG. 29. As can be observed from the figure, there are indeed variations in the cell surface densities depending on the lateral position on the surface. These variations do not appear to be significant as long as one measures along the central line of the chamber. The variation in cell density on the surface along the longitudinal line was also measured, by taking images at different positions along this line. This variation was about 5%, compared to the expected value of 3% for the Poisson statistics. The higher variation of 5% may be caused by an initial heterogeneity of cells in the sample, inaccuracies in the chamber dimensions, lack of homogeneity in magnetic configuration or by the image analysis itself.

Accuracy

Figure 30:
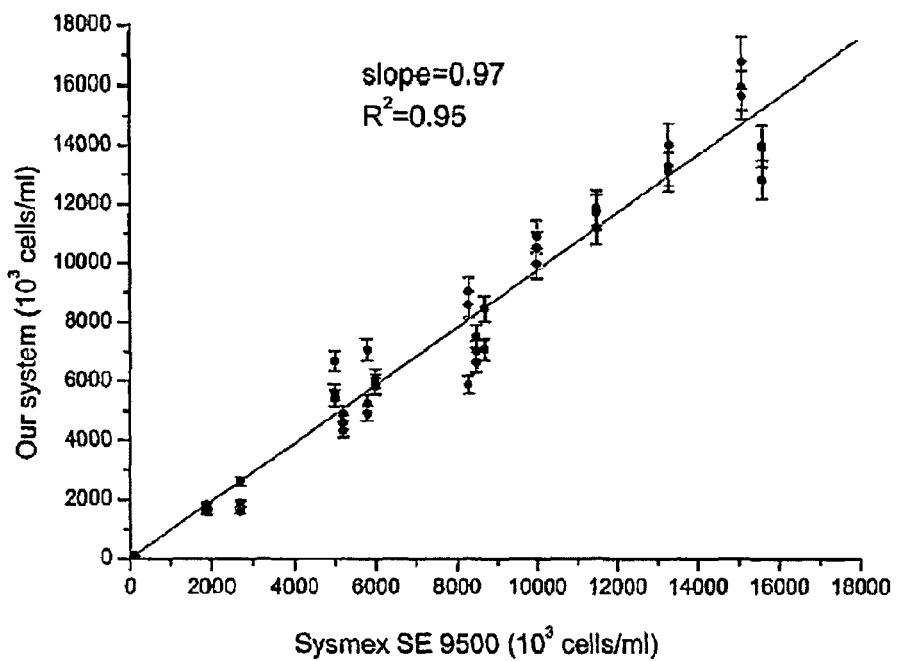
FIG. 30: Correlation between the absolute leukocyte count between the imaging system and the Sysmex® hematology analyzer. A slope of 0.97 with $R^2=0.95$ was found for cell counts ranging from 100 cells/µl to 16,000 cells/µl.

In this experiment, the accuracy of the system with respect to cell counting was evaluated by correlating the cell counts of 15 different blood samples to the data obtained by a commercial haematology analyser. Fifteen EDTA-anti-coagulated blood samples from different patients were collected and analyses were performed on the same day. From each sample an aliquot was taken for analysis in a 5-part differential haematology analyser (Sysmex® SE 9500, Sysmex® Corp., Long Grove, Ill.) and an aliquot for analysis on the described system. To 100 µl of EDTA anti-coagulated whole blood in a 12×75 mm glass tube, 40 µl 25 µg/ml biotinylated CD45 monoclonal antibodies were added. After 30 minutes of incubation at room temperature, 25 µl of 0.4 mg/ml streptavidin-ferrofluid was added. Then, the sample was placed in and out of the magnetic quadrupole (QMS13, Immunicon Corp., PA) three times for 10 seconds each time. After standing for another 30 minutes, 5 µl of 3 mg/ml acridine orange was added and the sample was diluted to a final volume of 2 ml with Cell Buffer (Immunicon® Corp). An aliquot of 320 µl of the sample was then inserted into the sample chamber. After capping the chamber, it was directly into the magnetic holder. After 10 minutes, three images were made at different positions on the surface of the chamber, and the number of cells in the images was measured using the cell counting software. The correlation between the counts on the cell analysis system and the counts on the haematology analyser was calculated. The correlation between the two systems is presented in FIG. 30. The $R^2$ was 0.95 and the regression line had a slope of 0.98 when the number of cells varied in the range of 100 and 15,000 cells/µl. The vertical error bars represent the measuring errors as discussed in the previous experiment.

EXAMPLE 3

CD4+Cell Counting

The number of CD4+ lymphocytes in 95% of all normal individuals fall between 355 to 1298 cells/µl. In AIDS patients, a CD4 count of 500 cells/µl is often used to initiate antiretroviral therapy, a count of 200 CD4/µl is used to start prophylactic anti-microbial treatment, a count of 100 CD4/µl is often associated with an increase in opportunistic infections and a count below 50 CD4/µl has a high occurrence of HIV related death. It is therefore important to accurately determine the number of lymphocytes expressing CD4.

Linearity

Figure 31:
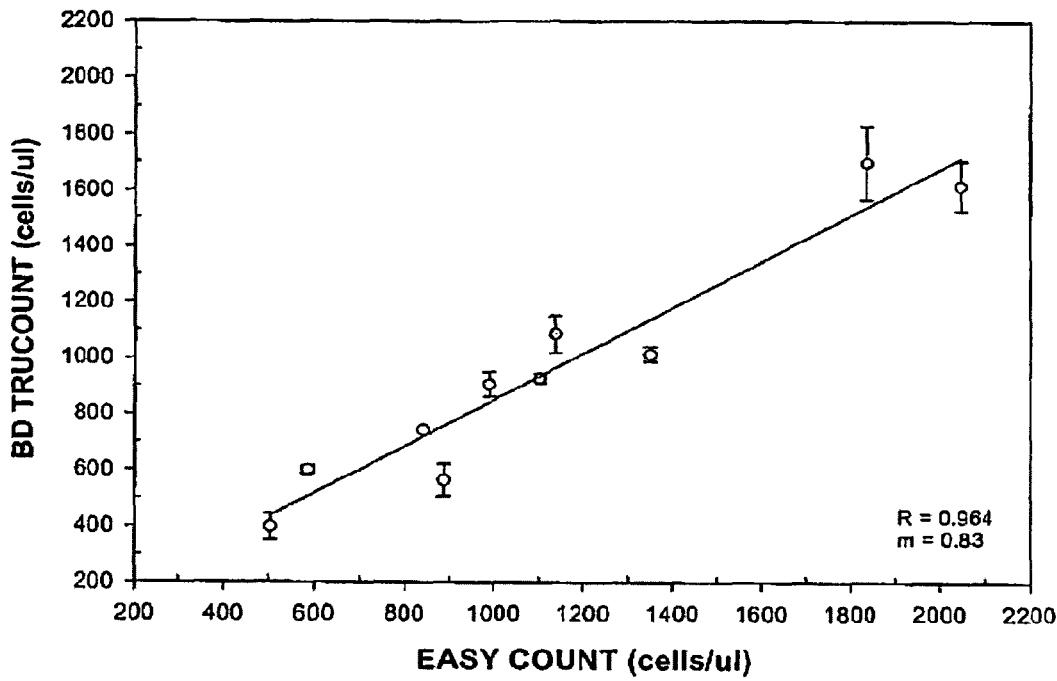
FIG. 31: Correlation of the CD4 count between the imaging system of the present invention and flow cytometric analysis using the BD Trucount® system.

CD4 counts were measured in whole blood samples from ten donors by Becton Dickinson's TruCount® flow cytometer and the method of the invention outlined below. Whole blood (200 µl) was added to 12 mm×75 mm polystyrene test tubes and mixed with 20 uL 0.1 mg/ml 10× biotinylated-anti-CD4 Mab (2 µg added Mab) and 8.5 µL 0.47 mg/ml Streptavidin ferrofluid (4 µg added iron). The sample was mixed and incubated for 10 minutes in a QMS13. After incubation 40 µl of 1 mM acridine orange dye (final concentration=20 µM) and 1731 µl of Cell Buffer, i.e. final volume=2 ml was added, mixed and ~350 µl of sample was placed into chamber. The chamber was inserted into magnetic yoke and after 10 minutes a count was obtained number (cells/µl) at 5 different chamber locations. The correlation coefficient R=0.96, the slope was 1.15 with an intercept of 53 indicating that the method of the present invention counted more cells than the reference method. The data are plotted in FIG. 31.

Discrimination Between CD4+Monocytes and Lymphocytes Based on Differences in Emissions The CD4 marker is expressed on both monocytes and lymphocytes. Therefore, using CD4 monoclonal antibodies for magnetic separation will result in the presence of both monocytes and lymphocytes on the chamber surface. To obtain absolute counts of both cell populations, it is possible to distinguish them on the basis of differences in staining with acridine orange. Acridine orange, the dye also used in the total leukocyte count, is known to be metachromatic. The dye shows a large shift in its emission spectrum when bound to double-stranded (ds) versus single-stranded (ss) nucleic acids (Table 2). Acridine orange binds to ds-nucleic acids by intercalation, and the intercalated form fluoresces green when excited by blue light. The maximum absorption of acridine orange bound by intercalation to DNA is at 500 to 506 nm and the emission is at 520 to 524 nm. Interaction of acridine orange with ss-nucleic acids is a complex, multi-step process initiated by acridine orange intercalation between neighboring bases, neutralization of the polymer charge by the cationic dye, and subsequent condensation and agglomeration (precipitation; solute-to-solid state transition) of the product. The absorption spectrum of acridine orange in these precipitated products is blue-shifted compared to that of the intercalated acridine orange, with maximum absorption ranging between 426-458 nm, depending on the base composition of the nucleic acid. The emission of acridine orange in these complexes also varies, between 630-644 nm, also depending on the base composition.

TABLE 2

Spectral characteristics of acridine orange
and Nucleic Acid-Dye Complexes.

| Dye or complex | Absorption maximum (nm) | Recommended excitation (nm) | Emission maximum (nm) |
|---|---|---|---|
| AO (monomer) | 492 | — | 525 |
| AO-ds DNA (intercalated) | 502 | 488 | 520-524 |
| AO-ss DNA (precipitated) | 426-458 | 457 | 630-644 |

Figure 32:
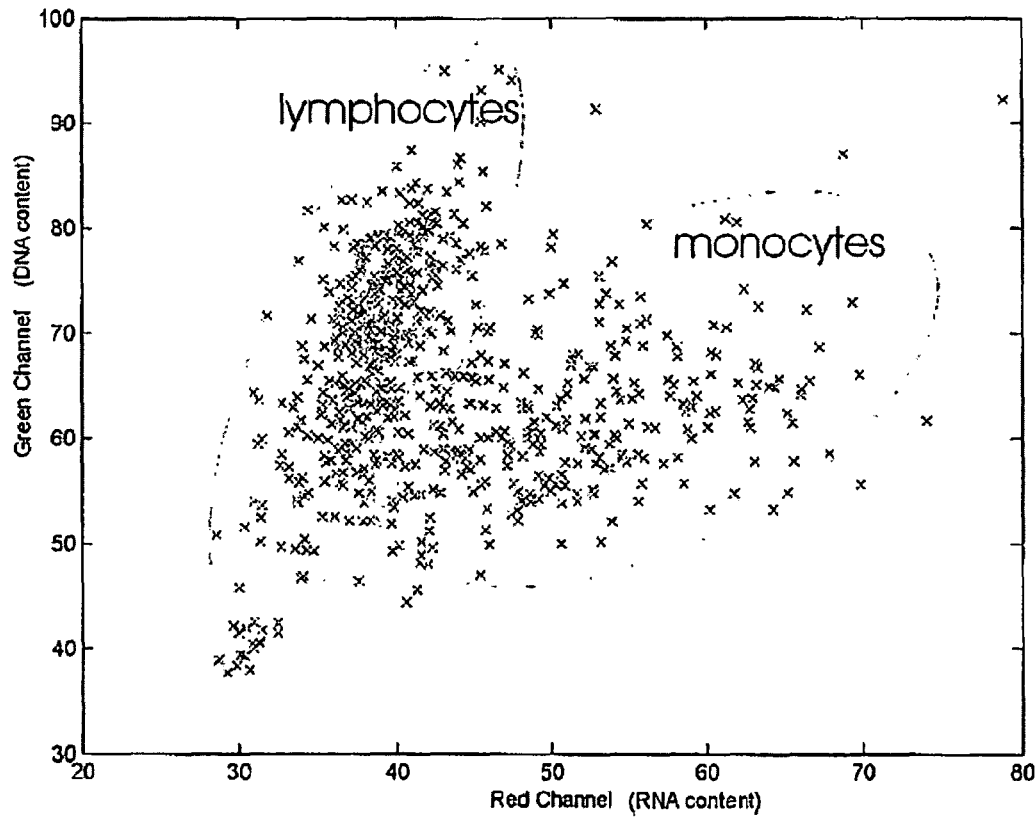
FIG. 32: Scatter plot of RNA content versus DNA content in cells separated with CD4-labeled magnetic particles. Two different clusters represent CD4+ lymphocytes and monocytes.

This metachromatic behavior of acridine orange can be used for distinguishing monocytes from lymphocytes, since monocytes have a larger amount of RNA than lymphocytes, although the concentration of the dye is also critical to obtain accurate differentiation. Therefore, the emission of acridine orange in the range of about 630-644 nm to is expected to be larger in monocytes than in lymphocytes. The following experiment was performed to investigate whether CD4+ monocytes and lymphocytes could be counted separately using a single labeling step by making use of the metachromaticity of acridine orange and the difference in RNA content of the two subpopulations of cells. The same labeling protocol was used as for total white blood cell counting, but now anti-CD4 monoclonal antibodies were used to label the CD4+ lymphocytes and monocytes instead of CD45 antibody. After the 10 minutes collection inside the magnetic separator, an image of the chamber surface was made using a 455df30 band-pass filter. In this image only the fluorescence of dye conjugated to the DNA content of the cells (which is also used for all white blood cells) is detected. Then another image was made using a 640df20 band-pass filter, which was used to measure the RNA content in the cells. The first image was used to locate the positions of all the cells, and these positions were stored in computer memory. In the second image, the average pixel intensity due to the RNA content of the cells at all positions was measured. FIG. 32 shows a scatter plot obtained from a sample of magnetically labeled CD4+ cells. The DNA content, measured as the average pixel intensity of cells in the image of the green channel, is plotted against the RNA content, measured as the average pixel intensity in the image of the red channel. Two populations can be distinguished, with monocytes having higher intensities in the red channel than lymphocytes. The number of monocytes and lymphocytes can be retrieved from the scatter plot as is commonly done in flow cytometry.

Figure 33:
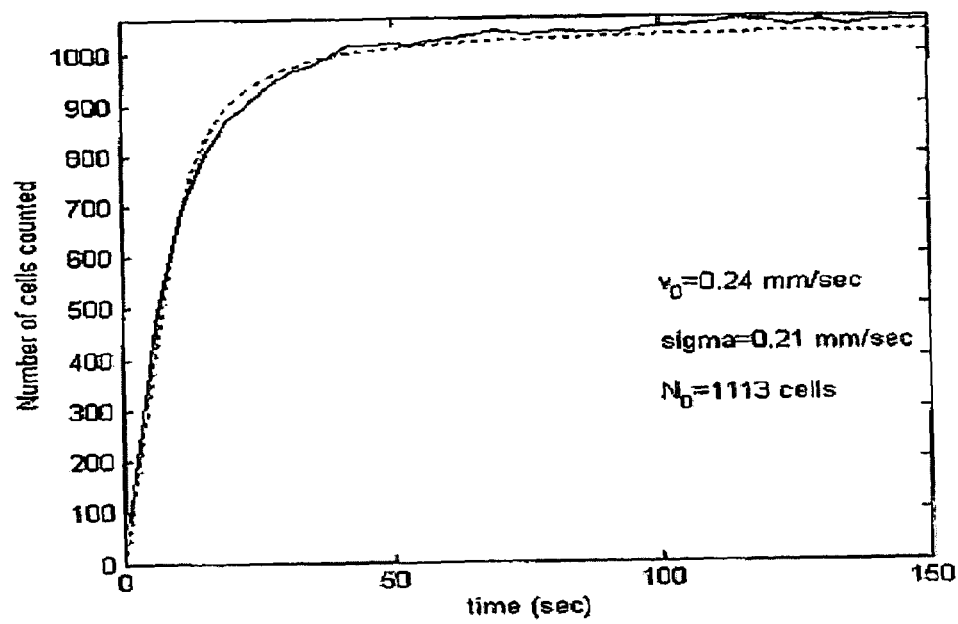
FIG. 33: Time trace of the number of cells in the image for a total white blood cell count. The model was fitted to the data which resulted in an average cell velocity $v_0=0.24$ mm/sec with a standard deviation of $\sigma=0.21$ min/sec for a cell total of $N_0=1113$.
Figure 34:
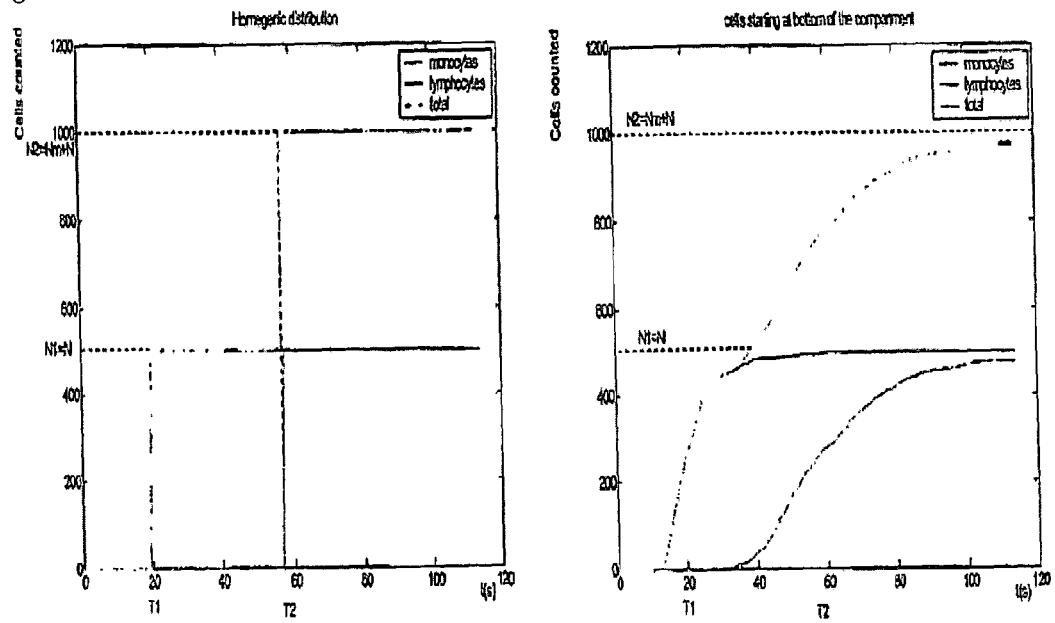
FIG. 34: N(t) of monocytes and lymphocytes for a homogeneous distribution.
$N_{monocytes}=N_{lymphocytes}=500$, $v_{monocytes}=0.2$ mm/sec; $v_{lymphocytes}=0.06$ mm/sec
(a) $\sigma_{monocytes}=$ lymphocytes$=0$
(b) $\sigma_{monocytes}=0.02$ mm/sec; $\sigma_{monocytes}=0.06$ mm/sec

Discrimination Between CD4+ Monocytes and Lymphocytes Based on Differences in Magnetic Loading/Antigen Density One can determine the average velocity of the cells during magnetic collection in the chamber, if the number of cells arriving at the surface is measured as a function of time. This can be done using a real-time image-processing algorithm that continuously processes the images obtained from the CCD camera. Such an algorithm was developed, enabling cell count measurements at a maximum rate of 0.25 images/sec. Based on the predicted dynamics (see Eq. 7), a time trace can be fitted to equation 7 to estimate the average velocity of the cells ($v_0$), the standard deviation of the velocity distribution ($\sigma$) and the total number of cells that were present in the volume under the imaged surface ($N_0$) prior to collection. FIG. 33 shows a typical time trace obtained in a total white blood cell count together with the result of a non-linear least-square fitting algorithm is shown (dotted line). The average velocity of the cells was estimated as $v_0$=0.24 mm/sec, the standard deviation $\sigma$=0.21 mm/sec and the total number of cells $N_0$=1113. Using this curve-fitting algorithm, it is possible to get an estimate of the total number (cells/μl), even if not all the cells are sufficiently magnetic to reach the surface. However, it must be noted that antigen expression (and thus the magnetic moment) may differ for subpopulations of leukocytes and the model may not be strictly applicable to all leukocyte populations without further refinements. When using monoclonal CD4+ antibodies to label the leukocytes magnetically, both CD4+ monocytes and lymphocytes are labeled. Since only the CD4+ lymphocyte count is clinically relevant in monitoring the progression of HIV-infection, methods are needed to distinguish the number of monocytes and lymphocytes in the total CD4+ count. Because the CD4 antigen expression is different on CD4+ monocytes and lymphocytes, the amount of magnetic labeling will also differ, thus resulting in a lower magnetic moment and lower mean velocity for the labeled monocytes. When counting the number of cells as a function of time, the number of monocytes and lymphocytes can be deduced from the shape of the N(t) curve. The normal antigen density on CD4+ lymphocytes is reported to be 47±14×10$^3$/cell, and 17±5×10$^3$/cell on CD4+ monocytes. Assuming that the same percentage of surface antigens on both monocytes and lymphocytes are occupied and that both have similar weight and shape, the antigen density can be related to their average collection rate. From earlier experiments, the average rate for CD4+ monocytes was found to be 0.2 mm/sec, thus predicting an average rate of 0.07 mm/sec for monocytes. In FIG. 34 the total cell count is shown, together with the number of monocytes and lymphocytes. If N1, N2, T1 and T2 are determined, $N_{monocytes}$ and $N_{lymphocytes}$ can be calculated as follows:

$$N_{lymphocytes} = \frac{N_2 T_1 - N_1 T_2}{T_1 - T_2}, N_{monocytes} = N_2 - N_1 \tag{37}$$

Figure 35:
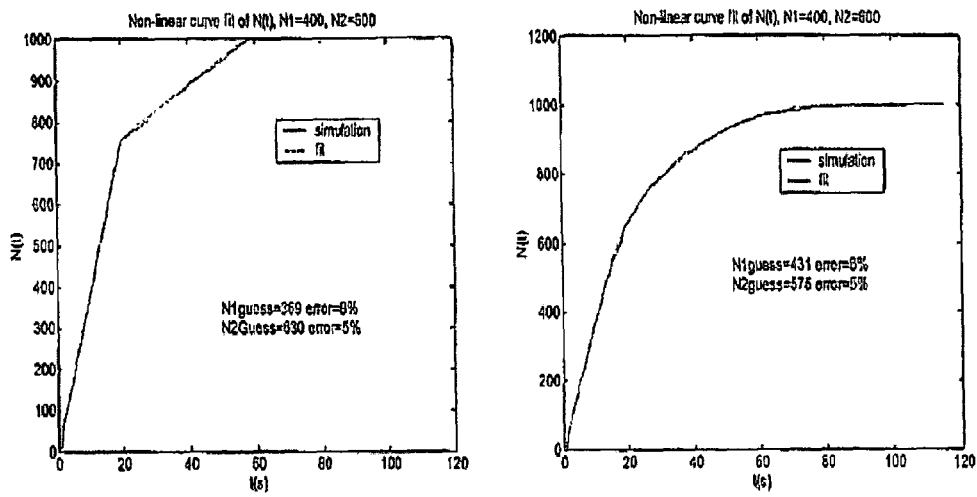
FIG. 35: Simulation and fit of N(t) of monocytes and lymphocytes for a homogeneous distribution. $N_{monocytes}=400$, $N_{lymphocytes}=600$ $v_{monocytes}0.07$ mm/sec, $v_{lymphocytes}=0.2$ mm/sec. (a) $\sigma_{monocytes}=0.002$ mm/sec, $\sigma_{lymphocytes}=0.006$
(b) $\sigma_{monocytes}=0.02$ mm/sec, $\sigma_{monocytes}=0.06$ mm/sec
Figure 36:
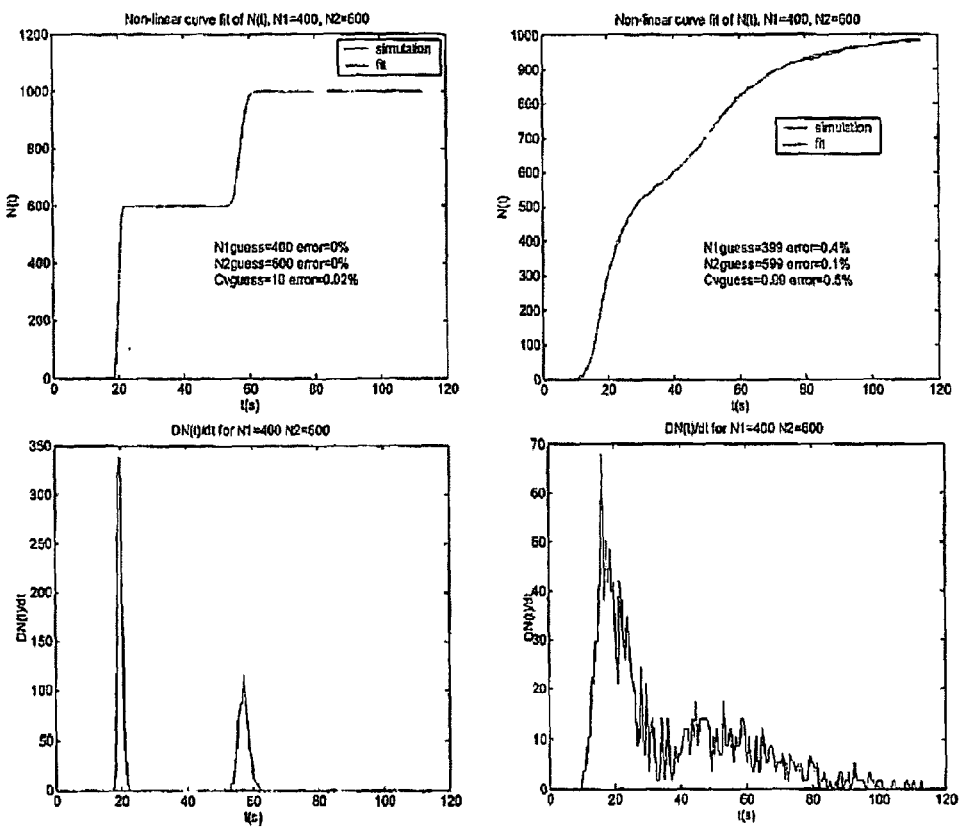
FIG. 36: N(t) and DN(t)/dt of monocytes and lymphocytes, with all cells starting at the bottom of the chamber.
$N_{monocytes}=400$, $N_{lymphocytes}=600$ $v_{monocytes}=0.07$ mm/sec, $v_{lymphocytes}=0.2$ mm/sec.
(a) $\sigma_{monocytes}=0.002$ mm/sec, $\sigma_{lymphocytes}=0.006$ mm/sec
(b) $\sigma_{monocytes}=0.02$ mm/sec, $\sigma_{monocytes}=0.06$ mm/sec

Using the standard deviation in antigen density, the standard deviation in the rates is predicted to be 0.02 mm/sec for monocytes and 0.06 mm/sec for lymphocytes. In FIG. 34b, the same cell count simulation is shown, with these deviations in the velocity. It is clear from the figure that the values of $N_1$, $N_2$, $T_1$ and $T_2$ cannot be determined accurately. A better option is to apply a non-linear curve fitting algorithm, based on the analytic solution of the N(t) for two cell-types. For one cell type, the solution is:

$$N(t) = \frac{1}{2}\left(\left(ysurf\sqrt{\pi} + tv0\mathrm{erf}\left(\frac{v0}{\sigma 0}\right)\sqrt{\pi} + \sigma 0 t e^{\left(-\frac{v0^2}{\sigma 0^2}\right)} + ysurf\sqrt{\pi}\,\mathrm{erf}\left(\frac{v0t - ysurf}{\sigma 0 t}\right) - \sqrt{\pi}\,v0t\mathrm{erf}\left(\frac{v0t - ysurf}{\sigma 0 t}\right) - \sigma 0 t e^{\left(-\frac{(v0t - ysurf)^2}{t^2 \sigma 0^2}\right)}\right) N0\right) / \left(ysurf\sqrt{\pi}\right) \tag{38}$$

where ysurf is the size of the chamber, v0 is the mean speed of the cells, σ0 is the deviation, and erf is the error function. This algorithm is based on the Newton iteration method. In FIG. 35 a (simulated) fit is shown, with $v_0$, $v_1$, $\sigma_0$ and $\sigma_1$ set as 'known', and N1 and N2 to be estimated. However, in real measurements one cannot assume that $v_0$ and $v_1$ are known accurately, due to dependence of v on the viscosity of the biological sample, differences in percentage of labeled surface antigens, and differences in the magnetic moment of the magnetic particles. Assuming all these relations are linear, the ratio of $v_0/v_1$ should remain constant. The fitting algorithm is therefore modified to also estimating a viscosity constant $C_v$, which is placed before $v_0$, $v_1$, $\sigma_0$ and $\sigma_1$. In FIG. 36, a simulation is shown with all labeled cells starting at the bottom of the compartment. This can be done by reversing the magnetic field for a sufficient time period. N1 and N2 can be estimated quite accurately from the figure.

When applying the same non-linear curve fitting method, the results are overall better than the curve fitting done with the homogeneous sample, as can be observed from FIG. 36. In this figure, the differential of the number of counted cells is also shown. While the Gaussian functions can be distinguished at low sigma values, the function with expected sigma is noisy due to large variations in cells arriving at the surface during the small time-segments that are used (0.57 sec).

Further means of discriminating the clinically relevant CD4+ lymphocytes from monocytes are enumerated below:
1. differential magnetic loading with magnetic particles of different sizes to enhance the migration rates of CD4+ lymphocytes;
2. optimizing the gap width in the magnetic arrangement and thus the magnetic field strength to increase the differential binding of CD4+ lymphocytes relative to monocytes;
3. adding free CD4 Mab to help inhibit CD4-specific magnetic particles from binding monocytes;
4. introducing non-magnetic beads that are specific for monocytes;
5. altering the antibody density on the magnetic capture particles to favor CD4+ lymphocytes; and
6. using an additional labeled CD45, e.g. anti CD45-fluorescein in combination with CD45 magnetic capture and Acridine orange to enhance lymphocyte detection.

EXAMPLE 4

Floodlight Direct Illumination

In a previously described embodiment, a LED generates the illumination light. The light passes through a condenser lens, a 455DF 70 bandpass-filter, and is reflected by a 515 DRLP dichroic mirror in the direction of the sample. The condenser lens focuses the light on the back focal plane of the objective, resulting in parallel illumination of the sample.

A straightforward way to eliminate most of the components is direct sample illumination, where the light of two LEDs is directly projected onto the sample. The performance compared to the previous system can be affected by a decrease in the intensity and homogeneity of the illumination, and an increase in the background signal.

Illumination Intensity and Homogeneity

Because the light is no longer focused, the illumination intensity is limited by the directivity of the LED. The LED that is currently used (NSPB500S, Nichia Corp., Japan) has a directivity ($2\theta_{1/2}$) of 30°. This means that the intensity decreases by 50% at a 15° angle of the LED axis.

Assuming a Gaussian intensity distribution, the normalized intensity distribution function $I(\theta)$ for (d<1) is given by:

$$I(\theta) = \frac{\sqrt{\ln(2)}}{\theta_{\frac{1}{2}}\sqrt{\pi}} \exp\left(\frac{-\ln(2)\theta^2}{\theta_{\frac{1}{2}}^2}\right) \tag{39}$$

The factor op the total light power (P/Ptot) projected onto a surface of size d (m) at a distance l(m) is:

$$\frac{P}{P_{tot}} = \left(\text{erf}\left(\frac{d\sqrt{\ln 2}}{2\theta_{\frac{1}{2}} l}\right)\right)^2 \tag{40}$$

One can also define a homogeneity-factor H as $H = I(\theta = \theta_{max})/I(\theta = 0)$, defining the ratio between the intensity at the center to the intensity at the edge of the surface.

$$H = \frac{I(\theta = \theta_{max})}{I(\theta = 0)} = \exp\left(\frac{-d^2\ln(2)}{4l^2\theta_{\frac{1}{2}}^2}\right) \tag{41}$$

Increased Background without Excitation Filter

A small portion of the emitted light of the LED (see FIG. 2.4) is in the spectral region of the emitted fluorescence of acridine orange (AO). Without using a low-pass filter, illumination light will be detected as a background in the fluorescent signal. A long-pass or band-pass filter (central wavelength 550 nm band pass 30 nm used in the previous illumination embodiment) can reduce this background. A 530 nm longpass filter was found to be optimal for the current illumination embodiment.

Implementation and Testing

The mathematical treatment above assumes a homogeneous illumination field of the LED, which is not very realistic; the structure of the LED and the focusing properties of the epoxy encapsulation produce a very irregular field at close range (<1 cm). Therefore, the optimal position is found empirically, at ~4 mm from the surface. Two LEDs were used in this setup, since this produces a more homogeneous illumination than a single LED. Also, higher illumination intensity can be reached. Depending on the illumination required by the application, more LEDs can be used.

To test the performance of both methods of illumination, they were tested using a solution of acridine orange and a non-fluorescent, absorbing sample. In both methods, the LEDs were driven at their maximum recommended current of 40 mA. The number of Digital Units as output from the CCD camera, as a measure of intensity, divided by the electrical energy consumption [DU's/Joule]. Since this value is dependent on the AO concentration in the sample, it can only be used for relative comparison. The minimum intensity divided by the maximum intensity that was found in the image, indicated in % (Fluorescent sample). The maximum intensity of the non-fluorescent sample, indicated in DU's.

TABLE 3 performance of both types of illumination

| Illumination Type | Efficiency (DU's/Joule) | Homogeneity (Imin/Imax * 100%) | Background level (DU's) |
|---|---|---|---|
| Epi illumination | 3.1 * 10³ | 80.2% | 10 |
| Direct illumination | 3.1 * 10³ | 80.5% | 12 |

The results are shown in Table 3 indicate that the efficiency and homogeneity are similar for both types of illumination, while the background level is slightly higher (2 DU's for the tested sample).

Other Embodiments

Further examples and applications of the algorithms and methods of this invention enable accurate cell enumeration, in a compact, rugged and low-cost system that is suitable for use in poor-resource settings. The performance of the system has been established in a number of clinically relevant applications including the analysis of blood cells, but numerous other applications can be envisioned. For example, as has been mentioned before, counting bovine leukocytes in milk (somatic cell count) may be an important application. The analysis of milk is currently performed by flow cytometry systems, requiring transport of the milk samples to specialized laboratories, which is both expensive and time consuming. The analyses described herein can be readily performed on-site, in a field setting, or in a conventional laboratory.

Further broadly defined applications include detection of bacterial, fungal and viral pathogens in humans or animals, water supplies, and air samples. Objects other than cells can also be counted by the system of the methods and algorithms of this invention by using appropriate fluorescent staining reagents. The system would be ideal for performing fast immunoassay analysis. For example, a magnetic particle specific for an analyte could be used for magnetic labeling, similar to the methods described for cells. A detectable label could then be added, such as a fluorescent polystyrene bead. As the magnetic particle-analyte-detectable label complex is magnetically manipulated to the observation surface, the instrument would be able to detect and enumerate the analyte.

The lack of fluidics or pumps, performance in sealed or sealable vessels and the compactness of the devices of this invention permits operation under low-g conditions and in confined spaces as prevail in space vessels and other extraterrestrial applications.

The preferred embodiments of the invention which incorporate these improvements, as described previously have also been found, unexpectedly, to enable the invention to be employed in many fields and applications additional to those cited above.

Other Applications

The following lists some of the potential applications of the system.

Research:
    General cell counter of immunological defined subsets in fluids, for example
        cell viability,
        CD20,
        B-lymphocytes;
        CD3 T-lymphocytes;
        CD8 Suppressor T-lymphocytes,
        CD14 monocytes,
        CD83 dendritic cells Hematology:
    Leukocyte Count (CD45)
    Granulocyte Count (CD15, monocytes differentiation based on lower antigen density)
    Left Shift (immature/mature granulocytes, based on CD64 antigen density)
    Shift reticulocytes (CD71)
    Progenitor Cell Count (CD34)
    Progenitor Cell Count (CD34)

Blood Banking:
    Residual leukocytes in red blood cell bags
    Progenitor cell count in leukopheresis products Cardiovascular disease:
    Activated platelet count (CD62P)
    Endothelial cell count (CD146)

Rheumatology:
    Cell subsets in joint aspirates

Infectious diseases:
    CD4 Count (HIV)
    Leukocyte/Epithelial/RBC cell count in sputum/urine
    Bacteria count in sputum/urine Environmental:
    Biological warfare agents Agriculture:
    Mastitis in cows (leukocytes in milk)

Outer Space Programs:
    Clinical analysis
    Environmental analysis

While particular embodiments of the present invention have been herein illustrated and described, they are not intended to limit the invention to such disclosure. Changes and modifications may be made therein and thereto within the scope of the following claims.

What we claim is:

1. An apparatus for detecting and enumerating a target cell population within a biological specimen, said apparatus comprising:
    a) an illumination means;
    b) a means for acquiring an image;
    c) a magnet arrangement having a spring loaded yoke assembly capable of receiving a sample chamber containing said biological specimen such that said sample chamber is positioned in a repeatable, accurate position, said magnet arrangement further being capable of allowing said sample chamber to be illuminated and imaged;
    d) a processor for performing one or more analytical algorithms on said image; and
    e) an output means for displaying results.

2. The apparatus of claim 1, wherein said illumination means is one or more light emitting diodes.

3. The apparatus of claim 2, wherein said light emitting diodes emit at a central wavelength of 470 nm.

4. The apparatus of claim 1, wherein said image acquiring means is selected from the group consisting of a digital camera and a CCD camera.

5. The apparatus of claim 1, wherein said sample chamber has a transparent observation surface.

6. The apparatus of claim 5, wherein said magnetic arrangement transports magnetically responsive members of said target cell population to said observation surface, magnetically responsive members are obtained by specifically labeling members of target cell population with magnetic particles.

7. The apparatus of claim 5, wherein said sample chamber is angled with respect to level to allow bubbles to float away from said observation surface.

8. A portable apparatus for performing low-cost, remote cell analysis, said apparatus comprising:
    a) an illumination means;
    b) a means for acquiring an image;
    c) a magnet arrangement having a spring loaded yoke assembly capable of receiving a sample chamber containing a biological specimen such that said sample chamber is positioned in a repeatable, accurate position, said magnet arrangement further being capable of allowing said sample chamber to be illuminated and imaged;
    d) a processor for performing one or more analytical algorithms on said image;
    e) an output means for displaying results; and
    f) a rechargeable battery.

* * * * *